US005871940A

United States Patent [19]
Hall et al.

[11] Patent Number: 5,871,940
[45] Date of Patent: Feb. 16, 1999

[54] ASSAYS FOR MODULATORS OF DROSOPHILA CATION CHANNEL FUNCTION

[75] Inventors: Linda M. Hall; Guoping Feng, both of Williamsville, N.Y.

[73] Assignee: Research Foundation of State University of New York, Amherst, N.Y.

[21] Appl. No.: 782,396

[22] Filed: Jan. 13, 1997

Related U.S. Application Data

[62] Division of Ser. No. 317,880, Oct. 4, 1994, Pat. No. 5,593,862.

[51] Int. Cl.$^6$ .............................. C12N 15/12; C12Q 1/02
[52] U.S. Cl. .............................. 435/7.21; 435/29; 435/7.2
[58] Field of Search .......................... 435/7.21, 29, 69.1, 435/7.2

[56] References Cited

U.S. PATENT DOCUMENTS

| 5,500,049 | 8/1996 | van der Ploeg et al. | 435/240.1 |
|---|---|---|---|
| 5,593,862 | 1/1997 | Hall et al. | 435/69.1 |
| 5,593,864 | 1/1997 | Arena et al. | 435/69.1 |
| 5,688,917 | 11/1997 | Arena et al. | 530/350 |

OTHER PUBLICATIONS

Auld, et al., "A rat brain Na$^+$channel with novel gating properties," *Neuron*, 1:449–461 (1988).
Catterall, "Cellular and molecular biology of voltage–gated sodium channels," *Physiol. Rev.*, 72:S2–S47 (1992).
Gantzky, "Neurogenetic analysis of Drosophila mutations affecting sodium channels: synergistic effects on viability and nerve conduction in double mutants involving tipE," *J. Neurogenet.*, 3:19–31 (1986).
Ganetzky, et al., "Neurogenetics of membrane excitability in Drosophila," *Annu. Rev. Genet.*, 20:13–44 (1986).
George, et al., "Molecular Cloning of an Atypical Voltage–gated Sodium Channel Expressed in Human Heart and Uterus: Evidence for a Distinct Gene Family," *Proc. Natl. Acad. Sci. USA*, 89:4893–4897 (1992).
Hall, "Genetics of the nervous system in Drosophila," *Quart. Rev. Biophys.*, 15:223–479 (1982).
Isom, "Auxillary subunits of voltage–gated ion channels," *Neurons*, 12:1183–1194 (1994).
Isom, et al., "Primary structure and functional expression of the b$_1$ subunit of the rat brain sodium channel," *Science*, 256:839–842 (1992).
Jackson, et al., "Two types of mutants affecting voltage–sensitive sodium channels in Drosophila melanogaster," *Nature*, 308:189–191 (1984).
Jackson, et al., "Genetic modification of voltage–sensitive sodium channels in Drosophila: gene dosage studies of the seizure locus," *J. Neurosci.*, 5:1144–1151 (1985).
Jackson, et al., "The tipE mutation of Drosophila decreases saxitoxin binding and interacts with other mutations affecting nerve membrane excitability," *J. Neurogenet.*, 3:1–17 (1986).

Kernan, et al., "nap$^{ts}$, a mutation affecting sodium channel activity in Drosophila, is an allele of mle, a regulator of X chromosome transcription," *Cell*, 66:949–959 (1991).
Krafte, et al., "Evidence for the involvement of more than one mRNA in controlling the inactivation process of rat and rabbit Na channels expressed in Xenopus oocytes." *J. Neurosci.*, 8:2859–2868 (1988).
Krafte, et al., "Inactivation of cloned Na channels expressed in Xenopus oocytes," *J. Gen. Physiol.*, 96:689–706 (1990).
Kulkarni, et al., "Temperature–sensitive paralytic mutations on the second and third chromosomes of Drosophila," *Genet. Res.*, 40:191–199 (1982).
Loughney, et al., "Molecular analysis of the para locus, a sodium channel gene in Drosophila," *Cell*, 58:1143–1154 (1989).
Nicholls, et al., "Ionic basis of the action potential," pp. 90–120, in *From neuron to brain*, Nicholls, et al., eds., Sunderland, Massachusetts: Sinauer Associates (1992).
Noda, et al., "Expression of Functional Sodium Channels from Cloned cDNA," *Nature*, 322:826–828 (1986).
Noda, et al., "Existence of Distinct Sodium Channel Messenger RNAs in Rat Brain," *Nature*, 320:188–192 (1986).
O'Dowd, et al., "Voltage–clamp analysis of sodium channels in wild–type and mutant Drosophila neurons," *J. Neurosci.*, 8:3633–3643 (1988).
O'Dowd, et al., "Alterations in the expression and gating of Drosophila sodium channels by mutations in the para gene," *Neuron*, 2:1301–1311 (1989).
Okamoto, et al., "Isolation of Drosophila genomic clones homologous to the eel sodium channel gene," *Proc. Japan. Acad.*, 63:284–288 (1987).
Papazin, et al., "Ion channels in Drosophila," *Ann. Rev. Physiol.*, 50:379–394 (1988).
Ramaswami, et al., "Two sodium–channel gene in Drosophila: implications for channel diversity," *Proc. Natl. Acad. USA*, 86:2079–2082, (1989).
Rosenthal, et al., "Amino Acid Sequence of a Putative Sodum Channel Expressed in the Giant Axon of the Squid Loligo opalescens," *Proc. Natl. Acad. Sci. USA*, 90:10026–10030 (1993).
Salkoff, et al., "Genetics of ion channels," *Physiol. Rev.*, 66:301–329 (1986).

(List continued on next page.)

*Primary Examiner*—David L. Fitzgerald
*Attorney, Agent, or Firm*—Nixon, Hargrave, Devans & Doyle LLP

[57] ABSTRACT

Genomic and cDNA clones corresponding to the tipE gen of *Drosophila melanogaster* are described. The tipE protein functions in concert with the para gene product, a polypeptide which exhibits similarity to mammalian voltage-dependent sodium channel α subunits but is not by itself functional. Coexpression of the tipE and para genes in a host cell affords functional cation channels. The invention accordingly provides screening assays for modulators of Drosophila cation channels employing cells expressing both tipE and para polypeptides, useful inter alia to evaluate candidate pesticidal agents.

13 Claims, 12 Drawing Sheets

OTHER PUBLICATIONS

Suzuki, et al., "Temperature–sensitive mutants in Drosophila melanogaster, VII. A mutation (pard$^{ts}$) causing reversible adult paralysis," *Proc. Natl. Acad. Sci. USA,* 68:890–893 (1971).

Tanouye, et al., "Genetics and molecular biology of ion channels in Drosophila," *Annu. Rev. Neurosci.,* 9:255–276 (1986).

Thackeray, et al., "Developmentally regulated alternative splicing generates a complex array of Drosophila para sodium channel isoforms," *J. Neuroscience,* 14:2569–2578 (1994).

Wu, et al., "A Drosophila mutant with a temperature–sensitive block in nerve conduction," *Proc. Natl. Acad. Sci. USA,* 75:4047–4051 (1978).

Wu, et al., "Neurogenetic studies of ion channels in Drosophila," pp. 261–314 in *Ion Channels,* vol. 3, Narahashi, ed., New York: Plenum Press (1992).

Gil et al., "Molecular Mapping and Cloning of the Drosophila TipE Locus—A Mutation Affecting Voltage–Sensitive Sodium Channels," *Abstracts—Society for Neuroscience, 4th Annual Meeting, Toronto, Canada, Nov. 13–18, 1988,* 14(2):835 (1989).

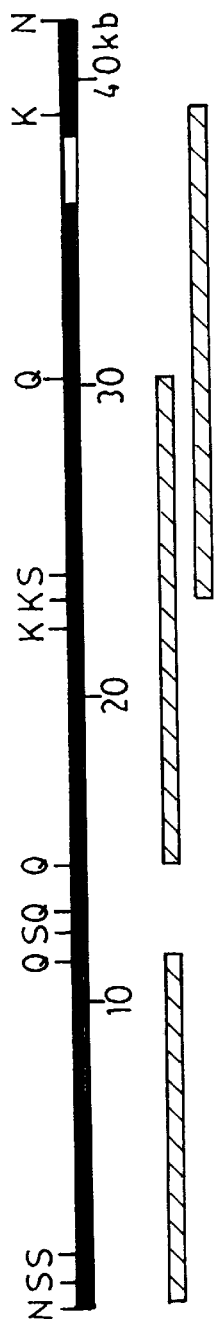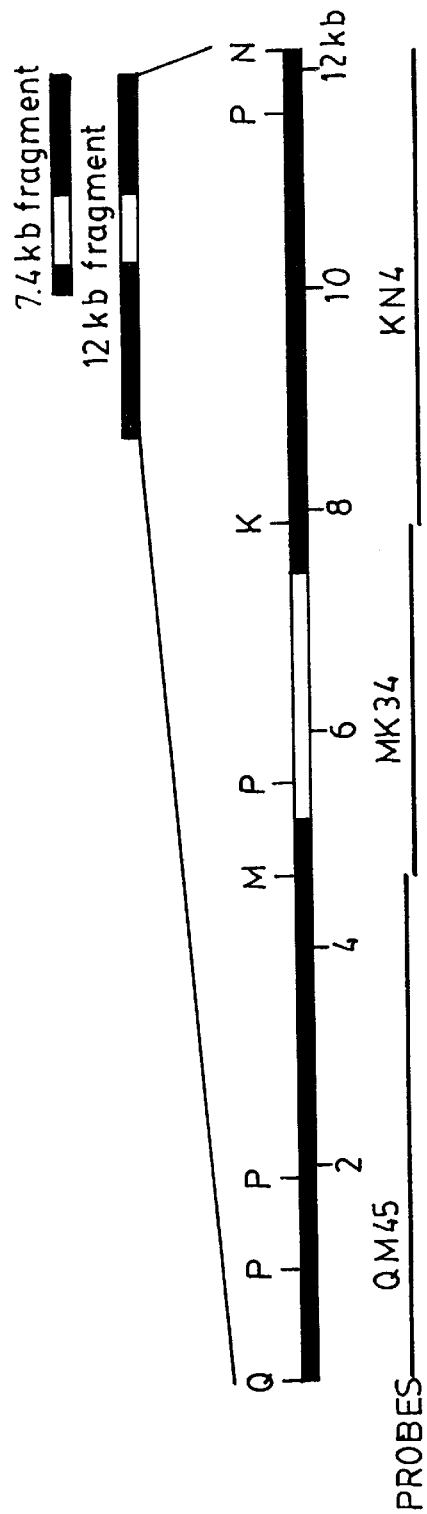
FIG.5A
FIG.5B

ASSAYS FOR MODULATORS OF DROSOPHILA CATION CHANNEL FUNCTION

This is a divisional of U.S. application Ser. No. 08/317,880, filed Oct. 4, 1994, now U.S. Pat. No. 5,593,862.

This invention was made through the support of the National Institutes of Health (Grant NS16204). The Federal Government may retain certain rights in the invention.

FIELD OF THE INVENTION

The present invention relates generally to a protein(s) required for expression of functional voltage dependent cation channels. More particularly, the present invention relates to the isolation and characterization of the tipE gene from *Drosophila melanogaster*, and methods of making same.

BACKGROUND OF THE INVENTION

Neuronal excitability is mediated by ion-specific channels which allow specific ions to cross cell membranes to generate action potentials. Voltage dependent sodium channels are responsible for the initial rising phase of the action potential (Nicholls et al., 1992, Ionic Basis of the Action Potential, pp. 90–120, edited by J. J. Nicholls, Sinauer Associates, Inc., Suderland, Mass.). In vertebrates, sodium channels in the brain, muscle and other tissues are large membrane glycoprotein complexes composed of an a subunit (230–270 kDa) and 1–2 tightly associated smaller (33–38 kDa) B subunits (reviewed by Catterall, 1992, Physiol. Rev., vol. 72, S2–S47). The large a subunit forms the ion permeable pore while the smaller subunits play key roles in the regulation of channel function (Isom et al., 1992, Science, vol. 256, 839–842; reviewed by Isom et al., 1994, Neuron, vol. 12, 1183–1194). The structure of invertebrate sodium channels has not been well defined. However, gene cloning studies establish the existance of α-subunits of structure similar to those described for vertebrates (Loughney et al., 1989, Cell, vol. 58, 1143–1154; Ramaswami and Tanouye, 1989, Proc. Natl. Acad. Sci. USA, vol. 86, 2079–2082; Okamoto et al., 1987, Proc. Jpn. Acad., vol. 63, 284–288).

Analysis of behavioral mutants provides a unique genetic approach to dissect the molecular components underlying neuronal membrane excitability without requiring any a priori information of the gene product (See reviews by Hall, 1982, Quart. Rev. Biophys., vol. 15, 223–479; Ganetzky and Wu, 1986, Annu. Rev. Genet., vol. 20, 13–44; Salkoff and Tanouye, 1986, Physiol. Rev., vol. 66, 301–329; Tanouye et al., 1986, Annu. Rev. Neurosci., vol. 9, 255–276; Papazian et al., 1988, Ann. Rev. Physiol., vol. 50, 379–394; Wu and Ganetzky, 1992, Neurogenetic Studies of Ion Channels in Drosophila, pp. 261–314 in Ion Channels, Vol. 3, edited by T. Narahashi, Plenum Press, New York). Therefore, this approach has the potential to identify new gene products which would not be isolated by biochemical methods or homology cloning.

One particular group of behavioral mutants, including para (paralytic, Suzuki et al., 1971, Proc. Nat. Acad. Sci. USA, vol. 68, 890–893), nap (no action potential, Wu et al., 1978, Proc. Natl. Acad. Sci. USA, vol. 75, 4047–4051), tipE (temperature-induced paralysis, locus E, Kulkarni and Padhye, 1982, Genet. Res., vol. 40, 191–199), and sei (seizure, Jackson, et al., 1984, Nature, vol. 308, 189–191; Jackson et al., 1985, J. Neurosci., vol. 5, 1144–1151), originally isolated by their phenotype of temperature-sensitive paralysis, has been proposed to affect sodium channels in Drosophila. For example, ligand binding studies with sodium channel-specific neurotoxins showed that head membranes from nap and tipE had a decreased number of saxitoxin binding sites, while different sei alleles affected the number or the affinity of saxitoxin binding sites (Jackson et al., 1984, cited elsewhere herein; Jackson et al., 1986, J. Neurogenet., vol. 3, 1–17). Whole cell patch clamp studies showed that cultured embryonic neurons from sei and tipE have reduced sodium currents (O'Dowd and Aldrich, 1988, J. Neurosci., vol. 8, 3633–3643), while para alleles have a decrease in the fraction of neurons which express sodium currents (O'Dowd et al., 1989, Neuron, vol. 2, 1301–1311). Molecular cloning of para revealed that it encodes a Drosophila sodium channel α subunit (Loughney et al., 1989, Cell, vol. 58, 1143–1154) while nap is a DNA binding protein which may regulate para expression by binding to the X chromosome where para is located (Kernan et al., 1991, Cell, vol. 66, 949–959).

The tipE mutation is an ethyl methane sulfonate-induced recessive mutation. Homozygous tipE flies paralyze rapidly at 38° and recover immediately when returned to 23° (Kulkarni and Padhye, 1982, cited elsewhere herein). Besides the results from ligand binding and electrophysiological studies discussed above, double mutant studies of tipE with para and nap provided additional evidence that tipE affects sodium channels. The combination of tipE with nap or tipE with various para alleles resulted in unconditional lethality of the double mutants at temperatures where single mutants survive (Jackson et al., 1986, cited elsewhere herein; Ganetzky, 1986, J. Neurogenet., vol. 3, 19–31). Interestingly, the synergistic interaction of tipE and para is allele-dependent. The combination of tipE with some para alleles allows varying degree of viability while with other alleles results in complete lethality. The observation that the allele-dependence is not correlated to the residual para sodium channel activities of the different alleles led to the speculation that tipE gene product may physically interact with para (Jackson et al., 1986, cited elsewhere herein; Ganetzky, 1986, cited elsewhere herein). Surviving double mutants of tipE with either para and nap are very weak, and exhibit enhanced temperature sensitivity for paralysis (Jackson et al., 1986, cited elsewhere herein; Ganetzky, 1986, cited elsewhere herein). The tipE and nap double mutants also displayed a greater reduction in saxitoxin binding activity than either single mutant homozygote (Jackson et al., 1986, cited elsewhere herein).

Although some types of sodium channel α-subunits alone are sufficient to form functional channels when expressed in Xenopus oocytes, their properties are not normal. Inactivation is slower and voltage dependence is shifted to more positive membrane potentials compared to channels in intact neurons. Coexpression of α-subunits with low molecular weight RNA from rat brain (presumably containing β1 and β2 subunits) not only corrected the abnormality but also dramatically increased the level of expressed sodium current (Auld et al., 1988, Neuron, vol. 1, 449–461; Krafte et al, 1988, J. Neurosci., vol. 8, 2859–2868; Krafte et al., 1990, J. Gen. Physiol., vol. 96, 689–706). Similar results were obtained when cloned β1 subunit was coexpressed with rat brain α-subunit (Isom et al., 1992, cited elsewhere herein).

Using a molecular genetic approach, it was determined that the para locus in Drosophila encodes the α-subunit of the voltage dependent sodium channel, and the entire para cDNA sequence was determined (Loughney et al., 1989, cited elsewhere herein; Thackeray and Ganetzky, 1994, J. Neuroscience, vol. 14, 2569–2578). In contrast to some rat brain sodium channel forms, expression of para sodium channel in Xenopus oocytes, or any other expression system, is undetectable. In fact, functional expression of a number of cloned sodium channels in heterologous expression systems has been weak or impossible. These difficult to express channels include those from squid (Rosenthal and Gilly, 1993, Proc. Natl. Acad. Sci. USA, vol. 90, 10026–10030), human heart and uterus (George, et al., 1992, Proc. Natl. Acad. Sci. USA, vol. 89, 4893–4897) and some forms from rat brain (Noda et al., 1986, Nature, vol. 322, 826–828; Noda et al., 1986, Nature, vol. 320, 188–192).

The inability to express insect sodium channel subunits with substantial purity and in an easy assayed system has inhibited the development of rapid and economical assays of sodium channel modulators. Sodium channel modulators have been investigated as insecticides, as therapeutic agents in the treatment and prevention of parasitic infections in humans and domestic animals, and as neuro-protective agents for the treatment of stroke, head injury and other ischemic events. The ability to rapidly screen potential modulators of insect sodium channels would also facilitate the development of compounds for the prevention and treatment of parasitic infections in humans, livestock and domestic animals.

For the foregoing reasons, there remains a need for a method of expressing and isolating a substantially pure form of the voltage dependent cation channel protein.

SUMMARY OF THE INVENTION

The primary object of the present invention, is the isolation and characterization of the gene encoding Drosophila melanogaster tipE protein, or a transcript thereof.

Another object of the present invention, is the production of a functional voltage dependent cation channel protein, using the tipE protein of the invention.

The present invention provides for the isolation and characterization of a gene comprising a DNA molecule(s) encoding tipE protein from Drosophila melanogaster. Positional cloning coupled with transformation rescue was used to identify and isolate the DNA molecule(s) of the invention. The DNA molecule(s) can comprise a cDNA encoding the Drosophila melanogaster tipE protein.

More particularly, the DNA molecule encoding the tipE protein, can comprise the nucleotide sequence, or a homolog or mutant thereof, as shown in Seq. ID. No. 1, and corresponding amino acid sequence as shown in Seq. ID. No. 2. The DNA molecule can be cloned into any suitable expression vector known in the art, to form a recombinant expression system which directs the expression of the tipE protein. Cells transformed with the recombinant vector are also provided.

In another aspect of the present invention, there is provided a purified functional voltage dependent cation channel protein, and method for its expression. More particularly, a method of expressing a functional voltage dependent cation channel is provided comprising, transforming a cell with the DNA molecule of the invention encoding tipE protein, and a second gene which encodes for a non-functional voltage dependent cation channel, under conditions which facilitate co-expression of tipE and the second gene, thereby forming a functional cation channel. The second gene can comprise any known voltage dependent cation channel, such as, for example, para and sei. It has been determined that those genes which can not express a functional voltage dependent cation channel, will in fact, express a functional cation channel in the presence of the tipE protein of the invention.

In a further aspect of the invention, there is provided a method of screening chemical agents for their effectiveness as pesticides using the tipE gene of the invention, or a transcript(s) thereof, or the tipE protein.

These and other features, aspects and advantages of the present invention will become better understood with reference to the following figures, description, and appended claims.

BRIEF DESCRIPTION OF THE DRAWINGS

FIG. 5A is a schematic representation of the cosmid clone rfi-6. Solid bars indicate DNA fragments which rescue tipE paralysis. Open areas within the solid bars indicate the location of the TE2 translocation/deletion. Striped bars represent DNA fragments which do not rescue tipE paralysis. The 7.4 kb fragment is from cosmid clone rfi-4. FIG. 5B is a schematic representation of the positions of transcripts relative to the TE2 translocation/deletion. The open box within the 12 kb solid bar indicates the location of the TE2 translocation/deletion. Dash lines indicate the uncertainty about the ends of transcripts. Arrow heads indicate the direction of transcripts determined by single stranded riboprobes.

DETAILED DESCRIPTION OF THE INVENTION

The present invention provides for the isolation and characterization of a gene comprising a DNA molecule(s) encoding tipE protein from $Drosophila$ $melanogaster$. Positional cloning coupled with transformation rescue was used to identify and isolate the DNA molecule(s) of the invention. The DNA molecule(s) can comprise a CDNA encoding the $Drosophila$ $melanogaster$ tipE protein.

Figure 7A:
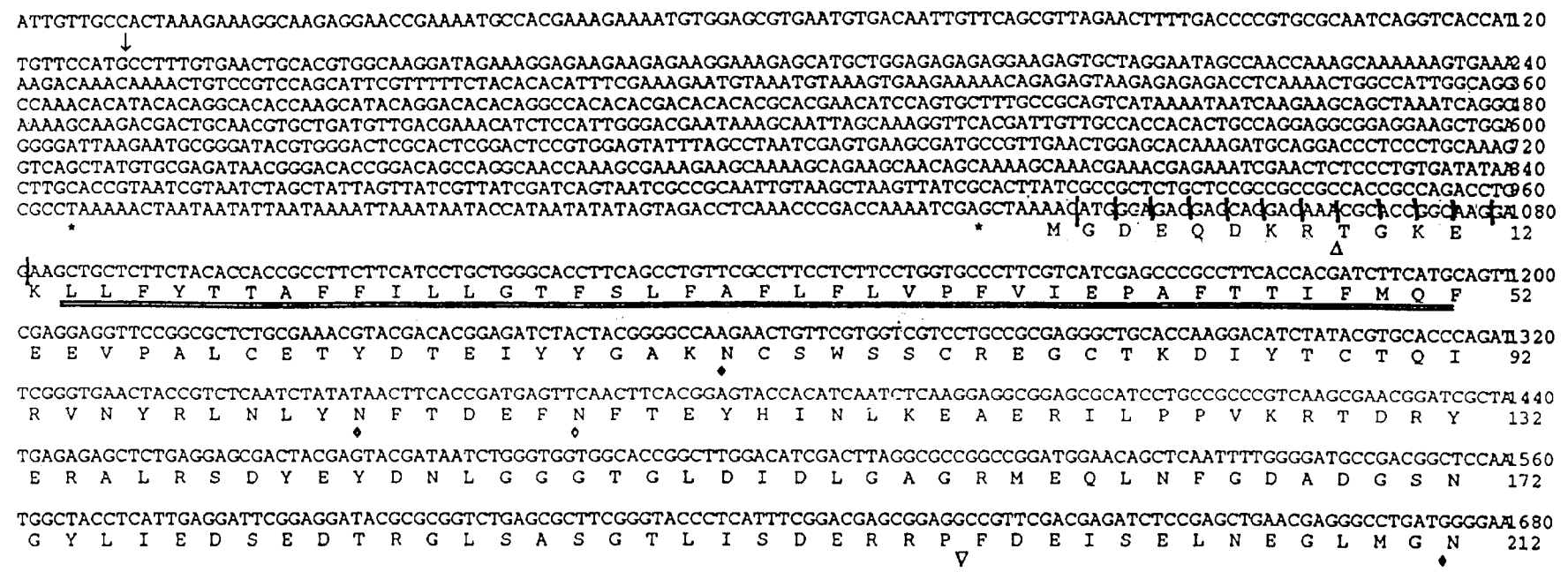
Figure 7B:
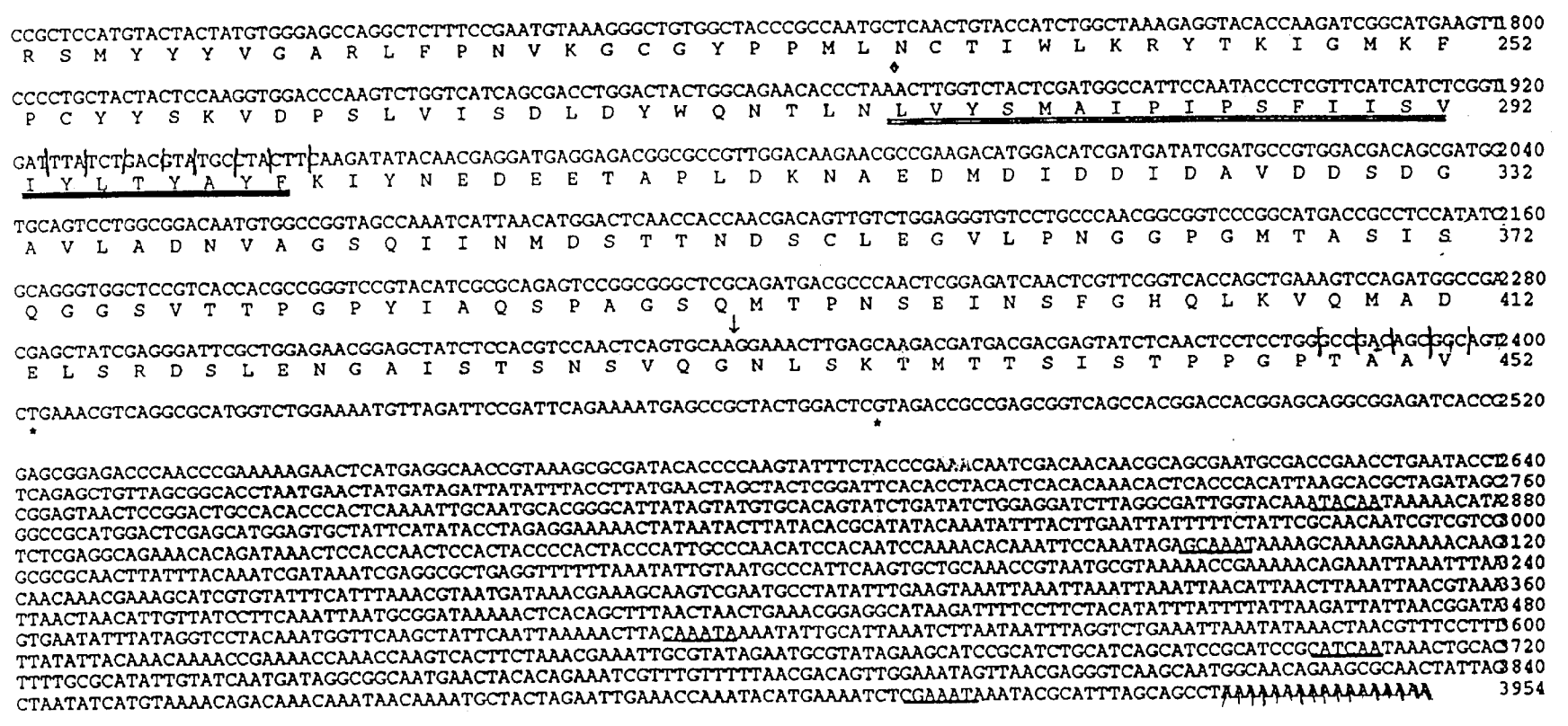
Figure 7C:
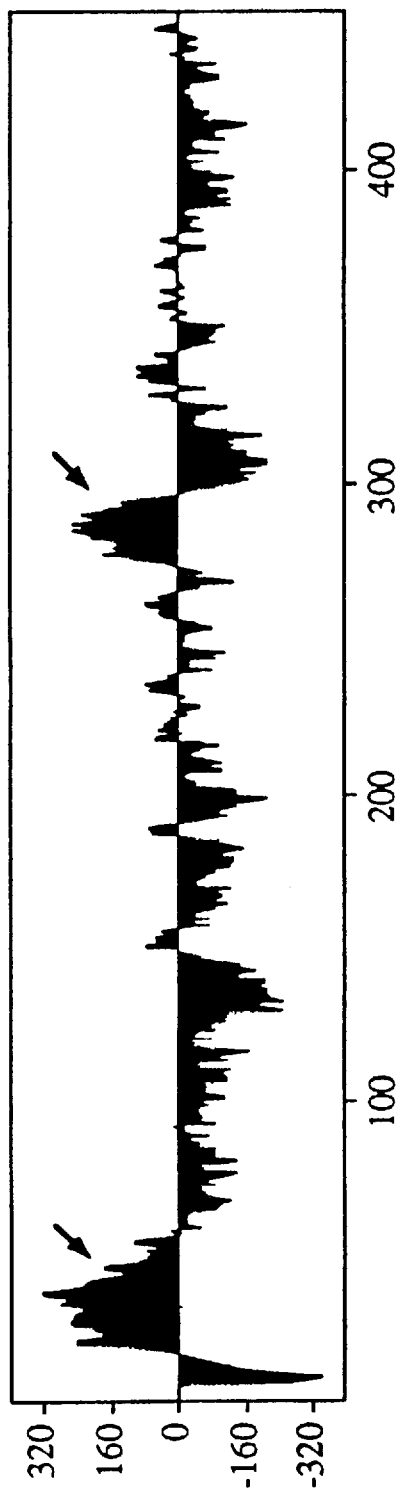
FIG. 7A illustrates the nucleotide and inferred amino acid sequences of tipE+, SEQ. ID NO. 1 and SEQ. ID NO. 2, respectively. Stop codons are indicated by (*). Proposed transmembrane domains are underlined. A potential PKC phosphorylation site is indicated by (Δ). Five potential N-glycosylation sites are marked by (◇). The positions of introns are indicated by (↓) above the sequence. (∇) indicates the location of the point mutation in tipE mutant flies.
FIG. 7B is a hydrophobicity plot of the deduced tipE amino acid sequence. Regions above the line indicate relative hydrophobicity. Proposed transmembrane domains are marked with arrows.

The DNA molecule of the invention preferably comprises cDNA encoding for an amino acid sequence, or mutant thereof, corresponding to SEQ. ID NO. 2, as shown in FIG. 7A. Preferably, the DNA molecule of the present invention comprises a nucleotide sequence, or a mutant DNA sequence thereof, corresponding to SEQ. ID NO. 1, as shown in FIG. 7A. It is understood that any modifications, i.e., insertions, deletions, mutations, recombinants, etc., of the DNA nucleotide and/or corresponding amino acid sequence(s) are within the scope of the present invention provided that the modified sequence(s) encode for a gene, its homologs or a fragment thereof producing tipE protein from $Drosophila$ $melanogaster$, or mutants thereof.

The isolation and characterization of the tipE protein, expressed from the DNA molecule of the invention is also provided. The tipE protein can be synthesized either in vivo or in vitro, using any standard technique in the art, such as, recombinant DNA expression, chemical synthesis or translation of isolated transcripts.

Recombinant DNA techniques are used to insert the DNA sequences of the invention into an appropriate expression vector, i.e., a vector which contains the necessary elements for the transcription and translation of the inserted coding sequences. A large number of vector systems known in the art can be used, such as plasmids, bacteriophage virus or other modified viruses. Suitable vectors include, but are not limited to the following viral vectors such as lambda vector system gtll, gtWES.tB, Charon 4, and plasmid vectors, such as pBR322, pBR325, pACYC177, pACYC184, pAR series, pKK223-3, pUC8, pUC9, pUC18, pUC19, pLG339, pR290, pKC37, pKC101, baculovirus vectors and other similar systems. The DNA sequences are cloned into the vector using standard cloning procedures in the art, as described by Maniatis et al., 1982, $Molecular$ $Cloning:$ $A$ $Laboratory$ $Manual$, Cold Spring Harbor Laboratory, Cold Spring Harbor, New York, which disclosure is hereby incorporated by reference.

The recombinant DNA molecule (e.g., vector+sequence of invention) can then be introduced into appropriate host cells, including but not limited to bacteria, insect cell lines, virus, yeast, mammalian cells, Xenopus oocytes, or the like. The vector system must be compatible with the host cell used. The recombinant vectors can be introduced into the host cells via transformation, transfection or infection using standard techniques in the art. A variety of host cell systems can be used to express the tipE gene of the invention. For example, host cell systems include, but are not limited to the following: bacteria transformed with bacteriophage DNA, plasmid DNA or cosmid DNA such as $E.$ $coli$ JM103, $E.$ $coli$ C600, $E.$ $coli$ C04, $E.$ $coli$ DH20 and $E.$ $coli$ TB1; microorganisms such as yeast containing yeast vectors; mammalian cell systems infected with virus (vaccinia virus, adenovirus, etc.); insect cell systems infected with virus (baculovirus).

In order to obtain efficient expression of the tipE gene, a promotor must be present in the expression vector. RNA polymerase normally binds to the promotor and initiates transcription of a gene or a group of linked genes and regulatory elements (operon). Promoters vary in their strength, i.e., ability to promote transcription. For the purpose of expressing the gene of the invention, it is desirable to use strong promoters in order to obtain a high level of transcription and, hence, expression of the gene. Depending upon the host cell system utilized, any one of a number of suitable promoters can be used, such as, the lac promotor, trp promotor, recA promotor, ribosomal RNA promotor, the PR and PL promoters of coliphage lambda and others including but not limited to lacUV5, ompF, bla, lpp and the like, nos promoter, the small subunit ribulose bisphosphate carboxylase genes, the polyhedron promoter from baculovirus, the small subunit chlorophyll A/B binding polypeptide, the 35S promoter of cauliflower mosaic virus, and promoters isolated from plant genes, including the Pto promoter itself (Vallejos et al., 1986, Genetics, vol. 112, pp. 93–105, which disclosure is hereby incorporated by reference) to direct high levels of transcription of adjacent DNA segments. Additionally, a hybrid trp-lacUV5 (tac) promotor or other *E. coli* promoters produced by recombinant DNA or other synthetic DNA techniques can be used to provide for transcription of the gene of the invention.

Bacterial host cell strains and expression vectors can be chosen which inhibit the action of the promotor unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the PL promotor of lambda can be induced by an increase in temperature in host cells containing a temperature sensitive lambda repressor, e.g., c1857. In this way, greater than 95% of the promotor-directed transcription may be inhibited in uninduced cells. Thus, expression of the gene of the invention can be controlled.

One such promotor/operator system is the so-called "tac" or trp-lac promotor/operator system (Russell and Bennett, 1982, Gene, vol. 20, pp.231–243, which disclosure is hereby incorporated by reference). This hybrid promotor is constructed by combining the −35 b.p. (−35 region) of the trp promotor and the −10 b.p. (−10 region or Pribnow box) of the lac promotor (the sequences of DNA which are the RNA polymerase binding site). In addition to maintaining the strong promotor characteristics of the tryptophan promotor, tac is also controlled by the lac repressor.

When cloning in a eucaryotic host cell, enhancer sequences (e.g., the 72 bp tandem repeat of SV40 DNA or the retroviral long terminal repeats of LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promotor elements (e.g., the polymerase binding site and the Goldberg-Hogness "TATA" box) which must be located immediately 5' to the gene, enhancer sequences have the remarkable ability to function upstream from, within, or downstream from eucaryotic genes. Therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 basis 5' to the initiation codon (ATG) to provide a ribosome binding site. Thus, any SD-ATG combination that can be utilized by host cell ribosomes can be employed. Such combinations include but are not limited to the SD-ATG combination from the CRO gene or the N gene of coliphage lambda, or from the *E. coli* tryptophan E, D, C, B or A genes. Additionally, any SD-ATG combination produced by recombinant DNA or other techniques involving incorporation of synthetic nucleotides can be used.

Any of the conventional cloning methods for insertion of DNA fragments into a vector can be used to ligate the promotor and other control elements into specific sites within the vector. Accordingly, gene sequences containing those regions coding for the tipE protein of the invention can be ligated into an expression vector at a specific site in relation to the vector promotor and control elements so that when the recombinant DNA molecule is introduced into a host cell the foreign genetic sequence can be expressed (i.e., transcribed and translated) by the host cell.

As previously mentioned, the recombinant DNA molecule can be introduced into appropriate host cells (including but not limited to bacteria, virus, yeast, insect cells, mammalian cells or the like) by transformation, infection or transfection (depending upon the vector/host cell system). Transformants are selected based upon the expression of one or more appropriate gene markers normally present in the vector, such as ampicillin resistance or tetracycline resistance in pBR322, or thymidine kinase activity in eucaryotic host systems. Expression of such marker genes should indicate that the recombinant DNA molecule is intact and is replicating. Expression vectors may be derived from cloning vectors, which usually contain a marker function. Such cloning vectors may include, but are not limited to the following: SV40 and adenovirus, vaccinia virus vectors, insect viruses such as baculoviruses, yeast vectors, bacteriophage vectors such as lambda gt-WES-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col E1, pSC101, pBR313, pML21, RSF2124, pCR1, RP4, pBR328 and the like.

The expression vectors containing the foreign gene inserts (e.g., DNA encoding the tipE protein of the invention) can be identified by three approaches: (1) DNA-DNA hybridization using probes comprising sequences that are homologous to the gene(s); (2) presence or absence of "marker" gene function and (3) expression of inserted sequences based on physical, immunological or functional properties. Once a recombinant which expresses the gene is identified, the gene product should be analyzed. Immunological analysis is especially important because the ultimate goal is to use the gene or recombinant expression systems that express the gene in assays for screening chemical agents. Once the tipE protein is identified, it is cultured under conditions which facilitate growth of the cells and expression of the gene as will be apparent to one skilled in the art, then isolated and purified by standard methods including chromatography (e.g., ion exchange, affinity, and sizing column chromatography), centrifugation, differential solubility, or by any other standard techniques.

In addition, since the amino acid sequence is known from the DNA sequence of the invention, the tipE protein can be synthesized by chemical methods according to the procedure of Hunkapiller et al., 1984, *Nature*, vol. 310, pp. 105–111, which disclosure is hereby incorporated by reference.

The invention also provides for biotechnology based pesticides and pharmaceutical agents which modulate the activity of voltage dependent cation channels. For example, overexpression of those portions of tipE protein of the present invention which interact with para (or those portions of para interacting with tipE) can block in vivo association between para and tipE, thereby preventing functional expression of the voltage dependent cation channel. Alternatively, the para tipE interaction may be blocked by expression of tipE antisense RNA or a ribozome directed against tipE MRNA, thereby preventing the development of functional cation channels.

As illustrated by Example XIV, below, the tipE protein(s) of the invention, or homologs thereof, may be used as a neuroprotective agents against stress events associated with voltage dependent cation channels, such as, for example, hypoxia, ischemia, stroke, and head trauma.

The present invention also provides for a transcript(s) isolated from the tipE gene of the invention. The transcripts can be synthesized using appropriate tipE mutant clones, by any conventionally known method in the art. The transcripts are translated either in vivo or in vitro. Cell-free systems can include wheat germ extracts and reticulocyte extracts. In vivo translation is preferable, with microinjection into frog oocytes being most preferred.

A substantially purified protein which functions as a voltage dependent cation channel is provided in accordance with the present invention. That is, for a functional voltage dependent cation channel to be expressed, a gene of the invention (e.g. DNA molecule encoding tipE), needs to be present during expression of the gene encoding the voltage dependent cation channel protein. Preferably the gene encoding the voltage dependent cation channel protein encodes the *Drosophila melanogaster* para protein, as described and sequenced by Loughney et al., 1989, cited elsewhere herein, and Thackeray and Ganetzky, 1994, cited elsewhere herein, which disclosures are hereby incorporated by reference, or difficult to express para homologues from other species, such as, for example, those from squid (Rosenthal and Gilly, 1993, Proc. Natl. Acad. Sci. USA, vol. 90, 10026–10030, which disclosure is hereby incorporated by reference), human heart and uterus (George, et al., 1992, Proc. Natl. Acad. Sci. USA, vol. 89, 4893–4897, which disclosure is hereby incorporated by reference) and some forms from rat brain (Noda et al., 1986, Nature, vol. 322, 826–828; Noda et al., 1986, Nature, vol. 320, 188–192, which disclosures are hereby incorporated by reference). The nature of the interaction between the tipE protein and the protein expressed by the gene encoding the voltage dependent cation channel protein is not intended to limit the instant invention. For example, purified biologically active para/tipE voltage dependent sodium channels may have a number of different physical forms. The para and tipE proteins may exist as full-length nascent or unprocessed polypeptides. Alternatively, they may exist as processed polypeptides or combinations thereof. The para and tipE proteins may be encoded by differently spliced transcripts leading to different protein isoforms having different amino acid sequences. The full-length nascent para and/or tipE protein may be postranslationally modified by specific proteolytic cleavage events which result in the formation of fragments of the full-length nascent protein. A fragment, or physical association of fragments may have full biological activity of the voltage dependent cation channel.

In order to obtain expression of a functional voltage dependent cation channel, the gene, or fragment thereof, encoding the tipE protein from *Drosophila melanogaster* is co-expressed with a gene encoding the voltage dependent cation channel protein. Preferably the gene encoding the voltage dependent cation channel protein encodes the para protein of *Drosophila melanogaster*. The nucleotide sequence of the gene encoding the *Drosophila melanogaster* para protein has been disclosed by Loughney et al., 1989, cited elsewhere herein, and Thackeray and Ganetzky, 1994, cited elsewhere herein, which disclosures are hereby incorporated by reference. It is readily apparent to those skilled in the art that a number of approaches could be used to assemble a full length cDNA. Suitable methods include assembling the available partial cDNAs into a full length cDNA, using the existing cDNA clones to screen a *Drosophila melanogaster* cDNA library to isolate a full length cDNA as described in Maniatis, cited elsewhere herein, which disclosure is hereby incorporated by reference, and PCR amplification of a full length cDNA using primers based on the published sequence as described in Innis et al., 1990, PCR Protocols: A Guide to Methods and Applications, Academic Press, San Diego), which disclosure is hereby incorporated by reference. It is also apparent to those skilled in the art that some modified combinations of the published sequences for para and its homologues, such as, for example, construction of different splice varient combinations and modification/truncation of 5' sequence regions or 3' sequence regions or both, may be desirable to ensure robust expression in conjunction with tipE.

It is understood that the functional voltage dependent cation channel of the present invention can be expressed by co-expression of the tipE gene and the voltage dependent cation channel gene in an appropriate host cell as previously described. Alternatively, transcript(s) of the tipE gene and voltage dependent cation channel gene can be synthesized and translated in vitro or in vivo.

The functional voltage dependent cation channel can also be prepared by expressing the voltage dependent cation channel gene in the presence of the isolated tipE protein. For example, such expression can be achieved in vivo by recombinant expression of an appropriate para vector in the presence of microinjected tipE protein or in a cell-free system by translation of a para transcript in the presence of tipE protein.

The functional voltage dependent cation channel produced in accordance with the present invention, can be used to screen for pesticides that are effective in the control of insects such as *Drosophila melanogaster*, and, particularly, pest isects The channels can also be used to screen pharmaceutical agents for their neuroprotective effect against, for example, hypoxia, ischemia, stroke and head trauma. Pesticide and pharmaceutical research has long been directed at voltage dependent cation channels. The availability of substantially purified proteins which function as voltage dependent cation channels facilitates the screening of such pesticides and pharmaceuticals for their ability to modulate voltage dependent cation channel activity. A preferred method for screening a chemical agent for effectiveness as a pesticide or pharmaceutical comprises the steps of transforming a host cell with a tipE gene of the present invention and a gene encoding a voltage dependent cation channel; facilitating co-expression of the tipE gene with the gene encoding the voltage dependent cation channel, thereby forming a functional voltage dependent cation channel; exposing the cell to a chemical agent having pesticidal or pharmaceutical activity; and evaluating the exposed cell to determine if the functional voltage dependent cation channel is the target site for the pesticidal or pharmaceutical activity of the chemical agent. Alternatively, the functional voltage dependent cation channel of the instant invention may be exposed, in vivo or in vitro, to the chemical agent, and the effect of the agent on voltage dependent cation channel activity evaluated by measuring cation current. Other exemplary methods of screening for pesticides and pharmaceuticals are described in Eldefrawei et al., 1987, FASEBj., vol. 1, pp. 262–271; and Rauh et al., 1990, Trends in Pharmacol. Sci., vol. 11, pp. 325–329, which disclosures are hereby incorporated by reference.

The present invention is further illustrated by the following examples.

EXAMPLE I

METHODS AND MATERIALS

1. Stocks and culture conditions:

Drosophila cultures were grown at 21° on standard cornmeal medium (Lewis, 1960, Drosophila News Service, vol. 34, 117–118, which disclosure is hereby incorporated by reference). The wild type Canton-S strain was obtained from J. C. HALL (Brandeis University). The tipE se strain carries tipE (3–13.5) linked to sepia (se, 3–15.5) a benign eye color mutation. By repeatedly backcrossing the tipE se strain to wild-type for ten generations, the tipE and se genes were placed in a wild-type genetic background. The multiply-inverted, dominantly-marked third chromosomes In (3LR) TM3, $y^+$ ri pP sep Sb $bx^{34e}$ $e^s$ Ser abbreviated as TM3 and In (3LR) TM6, $ss^-$ $bx^{34e}$ e Tb ca abbreviated as TM6 carry the $tipE^+$ allele. These chromosomes were used to balance the γ-ray induced mutant chromosomes. The deletions Df(3L)HR277 and Df(3L)HR298, isolated as described in Wohlwill and Bonner, 1991, cited elsewhere herein, which disclosure is hereby incorporated by reference, were provided by A. Wohlwill (University of Illinois, Chicago). The Df $(3L)x^{37}$ and $Df(3L)ems^{13}$ stocks were isolated by M. Simon (Stanford University) in accordance with Lindsley and Zimm, 1992, The Genome of *Drosophila melanogaster*, Academic Press, San Diego, which disclosure is hereby incorporated by reference. Df(3L)GN34 and Df(3L)GN19 were isolated by R. Rawson. The deficiencies HR277, HR298, X37 and ems13 were obtained from J. Fristrom (University of California, Berkeley). Description of the marker mutations and chromosomes used in the genetic studies can be found in Lindsley and Grell, 1968, Genetic Variations of *Drosophila melanogaster*, Carnegie Inst. Wash. Publ. No. 627, which disclosure is hereby incorporated by reference.

2. Mutagenesis:

The most important strains for positional cloning, Df(3L) TE1, Df(3L)TE3 and T(2;3)TE2, were isolated according to the following method. Wild-type males were mutagenized by irradiation with γ-rays at a dosage of 4000 rad. About 10 mutagenized males were mated to about 20 tipE se virgin females. The $F_1$ progeny were screened for temperature-sensitive paralytic flies by placing all the $F_1$ flies (1500–2000 flies per test) onto a shelf in a preheated plexiglass box (Williamson, 1971, Dros. Inf. Serv., vol. 46, 148–149, which disclosure is hereby incorporated by reference) at 38° for less than 8 min. Paralyzed flies were trapped on the shelf while mobile flies drowned in a mixture of vinegar and detergent at the bottom of the box. Individual paralyzed flies that recovered were crossed to TM3/$ap^{Xa}$ flies to balance the putative mutant chromosomes against TM3. The balanced chromosomes were retested for failure to complement tipE. The TE3 chromosome was recovered as a T(Y;3) translocation and was maintained over tipE se.

3. Cytological analysis:

Males from strains to be examined were crossed to wild-type virgin females. Salivary glands were dissected from third instar larvae in 0.8% saline solution, rinsed by dipping in 45% acetic acid, stained for 2 min. in lacto-acetic-orcein and squashed according to Engels et al., 1985, Focus, vol. 8, 6–8, which disclosure is hereby incorporated by reference. The squashes were examined using phase contrast optics and chromosome band assignments were made referring to Lefevre, 1976, pp. 31–36 in The Genetics and Biology of Drosophila, vol. 1A, edited by M. Ashburner and E. Novitski, Academic Press, London, which disclosure is hereby incorporated by reference.

4. In situ hybridization to polytene chromosomes:

Males from strains carrying chromosome aberrations were crossed to wild-type virgins and the offspring were grown at 18°. Chromosome squashes were prepared from third instar larvae according to Engels, et al., 1985, cited elsewhere herein, which disclosure is hereby incorporated by reference. DNA probes were biotinylated by nick translation using biotin-14-dATP and the BioNick Labeling System (GIBCO-BRL). Hybridization was conducted as described by Engels, et al., 1985, cited elsewhere herein, which disclosure is hereby incorporated by reference, with minor modifications (Murtaugh et al., 1993, Biochemistry, vol. 32, 6011–6018, which disclosure is hereby incorporated by reference).

5. Screening libraries:

The iso-1 cosmid library (a generous gift of J. W. Tamkun, University of California, Santa Cruz) was constructed in Not-Bam-Not-CoSpeR vector ready for germline transformation (Tamkun et al., 1992, Cell, vol. 68, 561–572, which disclosure is hereby incorporated by reference). Standard methods were used to plate the library and transfer the DNA to nylon membranes (Sambrook et al., 1989, Molecular Cloning: A Laboratory Manual, Cold Spring Harbor Laboratory Press, New York, which disclosure is hereby incorporated by reference). Hybridization was 16 hours at 65° in 50 mM $NaH_2PO_4$ pH7.0, 5× SSC, 5× Denhardt's, 0.25% SDS and 0.1 mg/ml denatured salmon sperm DNA with $^{32}$P-labeled DNA probes at a concentration of $10^6$ cpm/ml. Membranes were washed 2 times for 15 min each at room temperature in 2× SSC, 0.1% SDS followed by 2 more washes for 30 min each at 65° in 0.1× SSC, 0.1% SDS. Membranes were exposed to X-ray film at −70°. Standard solutions (SSC, Denhardt's, etc.) are as described by Sambrook et al., 1989, cited elsewhere herein, which disclosure is hereby incorporated by reference.

6. Genomic Southern blots:

Genomic DNA was isolated using a rapid DNA isolation method (Jowett, 1986, Preparation of Nucleic Acids, pp. 275–277 in Drosophila: A Practical Approach, edited by D. B. Robert, IRL Press, Oxford, which disclosure is hereby incorporated by reference). Twenty μg of genomic DNA was used for a typical restriction enzyme digestion and genomic Southern blot. The digested DNA was fractionated on 0.7% agarose gels. Gels were denatured and capillary transferred to ICN nylon membranes according to manufacturer's protocol and fixed by UV crosslinking using UV STRATALINKER™ 2400 (Stratagene). Hybridization and wash conditions are as described in library screening.

7. RNA preparation and Northern blots:

Heads, bodies and leg/antena fractions were isolated from frozen adult flies as previously described in Schmidt-Nielsen et al., 1977, J. Neurochem., vol. 29, 1013–1029, which disclosure is hereby incorporated by reference. Total RNA was prepared by guanidinium isothiocyanate-CsCl gradient method and poly($A^+$) RNA was selected by a single oligo (dT)-cellulose (Type II, Collaborative Research Inc.) column chromatography (Sambrook et al., 1989, cited elsewhere herein, which disclosure is hereby incorporated by reference). Ten μg of poly($A^+$) RNA were loaded in each lane. Preparation of blots and hybridization conditions are described in Zheng et al., 1994, J. Neurosci., in press, which disclosure is hereby incorporated by reference. To standardize for mRNA recovery and loading differences, blots were reprobed with a 0.6 kb rp49 cDNA fragment, a gene encoding a ribosomal protein which is uniformly expressed (O'Connell and Rosbach, 1984, Nucl. Acids Res., vol. 12, 5495–5513, which disclosure is hereby incorporated by reference).

8. Polymerase chain reaction (PCR):

The 100 μl PCR reaction mixture contained: 1× PCR buffer (10 mM Tris-HCl pH8.3, 50 mM KCl, 1.5 mM $MgCl_2$, 0.001% gelatin), 0.2 mM of each of the dNTPs, 0.1 μM of each primer, 300 ng genomic DNA and 1.25 units AMPLITAQ™ DNA polymerase (Perkin Elmer Cetus). Following an initial 2 min at 94°, the following cycle was repeated 35 times: denaturation 2 min at 94°, annealing 1 min at 60°, extension 2 min at 72°. The final extension was 10 min at 72°. Ten μl of each PCR product was analyzed on a 1.2% agarose gel. For PCR with Pfu DNA polymerase (Stratagene), annealing temperature was 55° C. and 2.5 units of Pfu were used.

9. Germline transformation:

The cosmid clone rfi-6 in CoSpeR P-element transformation vector was used directly for transformation. For other transformations with the genomic DNA fragments from cosmid clones, restriction fragments were subcloned into the P-element transformation vector pCaSpeR2 (Thummel and Pirrotta, 1992, Dros. Inf. Serv., vol. 71, 150, which disclosure is hereby incorporated by reference). Both CoSpeR and pCaSpeR2 transformation vectors contain the mini $w^+$ (orange to red eye color) marker. DNA from these constructs was mixed with the helper plasmid p(D2,3), a source of P-element transposase (a generous gift from D. Ready, Purdue University, prepared in accordance with Laski et al., 1986, Cell, vol. 44, 7–19, which disclosure is hereby incorporated by reference), at a concentration of 1:0.25 μg/μl (construct:helper plasmid) and injected into w;tipE se homozygous embryos. Surviving $G_o$ adults were crossed to w;tipE se homozygotes and their progeny were screened for $w^+$ transformants. Transformants bearing single copy of construct DNA in homozygous tipE background were tested for paralysis at 38° for 2 min.

10. Drosophila Paralysis Test:

Paralysis tests were conducted by submerging glass vials containing flies into 38° C. water bath for 2 min.

11. Screening Libraries:

The Drosophila head cDNA library was generously provided by P. Salvaterra (Itoh et al., 1985). Hybridization was 16 hours at 65° C. in 50 mM $NaH_2PO_4$ pH7.0, 5× SSC, 5× Denhardt's, 0.25% SDS and 0.1 mg/ml denatured salmon sperm DNA with $^{32}$P-labeled DNA probes at a concentration of $10^6$ cpm/ml. Membranes were washed 2 times for 15 min each at room temperature in 2× SSC, 0.1% SDS followed by 2 more washes for 30 min each at 65° C. in 0.1× SSC, 0.1% SDS. Membranes were exposed to X-ray film at −70°. Standard solutions (SSC, Denhardt's) are as described by Sambrook et al., 1989, cited elsewhere herein, which disclosure is hereby incorporated by reference.

12. DNA Sequencing and Data Analysis:

Inserts from phage cDNA clones were cut out with EcoRI and subcloned into pBluescript II SK- vector (Stratagene) using T4 DNA ligase (New England Biolabs). Nested deletion was performed following the procedure of Henikoff, 1987, Methods in Enzym., vol. 155, 156–165, which disclosure is hereby incorporated by reference. Double stranded DNA sequencing was performed on an Applied Biosystem Sequencer Model 373A using the dideoxy chain termination method with fluorescent-dye tagged M13 or M13 reverse primers according to instructions supplied with a Taq Dye Primer sequencing kit (Applied Biosystem, Inc.). Each segment of DNA was sequenced at least twice in both directions. To sequence genomic DNA from wild-type and tipE mutants, primers with M13 or SP6 sequence tagged to 5' ends were synthesized using sequence information from cDNA clones. Sequencing templates were generated by PCR, under conditions described below, using genomic DNA either from wild-type or mutants as template. PCR products were purified with Centricon-100 (Amicon) prior to sequencing. Double stranded DNA sequencing was performed as described above. DNA contig assembly used Geneworks software (Intelligenetics, Inc.). All other sequence analysis was performed with GCG program from Wisconsin Genetics Computer Group (Devereux et al., 1984, Nucl. Acids Res., vol. 15, 1353–1361, which disclosure is hereby incorporated by reference).

13. In situ Hybridization to Embryo Whole Mounts:

Whole mount in situ hybridization to Drosophila embryos followed the procedure of Tautz and Pfeifle (1989). A 272 bp (position 1761–2032 in FIG. 2) single-stranded digoxigenin-labeled cDNA probe was used. The probe was prepared as described by Zheng et al., 1994, cited elsewhere herein, which disclosure is hereby incorporated by reference.

14. RNA Preparation and Northern Blots:

Samples from different developmental stages were collected and synchronized at 25° C. as described by Roberts, 1986, Basic Drosophila Care and Techniques, pp. 1–38 in Drosophila: A Practical Approach, edited by D. B. Roberts, IRL Press, Oxford, which disclosure is hereby incorporated by reference. RNA was prepared by guanidinium isothiocyanate-CsCl gradient method, and poly($A^+$) RNA was selected by a single oligo(dT)-cellulose (Type II, Collaborative Research Inc.) column chromatography (Sambrook et al., 1989, cited elsewhere herein, which disclosure is hereby incorporated by reference). Ten μg poly ($A^+$) RNA was loaded in each lane. Preparation of blots and hybridization conditions are the same as described by Zheng et al., 1994, cited elsewhere herein, which disclosure is hereby incorporated by reference. To standardize for mRNA recovery and loading differences, blots were reprobed with a 0.6 kb rp49 cDNA fragment, a gene encoding a ribosomal protein which is widely expressend (O'Connell and Rosbash, 1984, cited elsewhere herein, which disclosure is hereby incorporated by reference). Signals on blots were quantitated using a Betascope blot analyzer (Betagen, Sullivan et al., 1987, Biotechniques, vol. 5, 672–678, which disclosure is hereby incorporated by reference).

15. Germline Transformation:

Germline transformation was done as described by Spradling, 1986, pp. 175–197 in Drosophila: A Practical Approach, edited by D. B. Robert, IRL Press, Oxford, which disclosure is hereby incorporated by reference. The 2 kb SspI fragment from the 4 kb cDNA clone was subcloned into the StuI site of pCaSpeR-hs vector containing a heat shock promoter (Thummel and Pirrotta, 1992, cited elsewhere herein, which disclosure is hereby incorporated by reference). This SspI fragment contains the whole ORF, 67 bp of 5' untranslated region and 558 bp of 3' untranslated region. The construct with the tipE point mutation was generated by replacing the KpnI/BstEII (from nucleotide 1615 to 2252, 638 bp) fragment with the equivalent fragment amplified from tipE mutant flies using PCR. The construct and point mutation was confirmed by sequencing. The transformation vector contains the mini $w^+$ (orange to red eye color) marker. DNA from these constructs was mixed with the helper plasmid p(D2,3), a source of p-element transposase (a generous gift from D. Ready, Purdue University, Laski et al., 1986, cited elsewhere herein, which disclosure is hereby incorporated by reference), at a concentration of 1:0.25 μg/μl (construct:helper plasmid) and injected into w;tipE se homozygous embryos. Injected flies were crossed to w;tipE se homozygotes and their progeny were screened for $w^+$ transformants.

16. Heat Shock Induction of tiPE Expression in Transformants:

Eggs from transformants with cDNA constructs were collected in a 1 hour period. Fifty eggs were placed in each food vial. Heat shock was conducted by submerging the vial in 35° C. water bath for 1 hour. To induce tipE gene expression in adults, flies were started to undergo heat shock within 12 hours of eclosion and repeated once a day up to 14 days. To induce tipE gene expression throughout developmental stages, heat shock was started 24 hours after egg laying and repeated once a day until eclosion. For "shift-up" experiment, heat shock was started at different developmental stages. Eggs were collected and kept at 21° C. The first vial of eggs was heat-shocked 24 hours after egg laying and treatment continued once a day until eclosion. Every 24 hour another vial of the collected eggs (or larvae or pupae later on as they developed) was heat shocked and treatment continued until eclosion. For "shift-down" experiment, all the egg vials were heat-shocked 24 hour after egg laying. Every 24 hour a vial was removed from the heat treated group and kept at 21° C. Flies were tested for paralysis within 12 hours of eclosion.

17. in vitro Translation:

The same SspI cDNA fragment for transformation was subcloned into EcoRV site of pBluescript II SK- vector. The tipE mutant clone was generated as described above. The constructs were linearized with SalI (for T3 RNA polymerase to make RNA) or NotI (for T7 RNA polymerase to make antisense RNA as a control). Transcripts were synthesized using T7 or T3 mMESSAGEmMACHINE kits (Ambion). These transcripts were translated in vitro in a rabbit reticulate lysate (Promega) either in the presence or absence of canine pancreatic microsomes (Promega) and labeled with $^{35}$S-methionine (at 0.8 mCi/ml with specific activity of 1016 Ci/mmol, Amersham). The translation product (5 µl, or equivalent after treatment) was analyzed by standard SDS-polyacrylamide gel electrophoresis. In some cases, the translation product was treated before loading onto gels. To treat at high pH, translated product was incubated in 10 volumes of 0.1M $NaCO_3$ (pH11.5) on ice for 30 min., then pelleted by centrifugation and rinsed with PBS before resuspending in gel loading buffer. For deglycosylation, 10 µl translation product was treated with 1000 units N-glycosydase F (New England Biolabs) in a 30 µl reaction using buffers and conditions recommended by manufacturer. For protelytic treatment, 1 µl (1 µg/µl) trypsin (type I from Sigma) was added to 10 µl translation product and incubated on ice for 3 hours either in the presence or absence of 0.1% Triton x100. The reaction was stopped by adding 2 µl (5 µg/µl) soybean trypsin inhibitor (Sigma).

18. Coexpression of tiPE and Para in XenoPus OocYtes:

Transcripts of tipE+ were synthesized as described for in vitro translation. Transcripts of tipE and para were mixed at a concentration of 0.1 mg/ml each for injection into oocytes. Stage V oocytes were removed from adult female Xenopus laevis, defolliculated with 2 mg/ml collagenase (Type I, Sigma) in OR solution (82.5 mM NaCl, 2.0 mM KCl, 1.0 mM $MgCl_2$, and 5.0 mM HEPES pH7.5) for 40 min. Defolliculated oocytes were injected with 50 nl in vitro transcribed RNA. Injected oocytes were incubated at 20° C. in 0.5x L-15 media (Sigma) in the presence of Penicillin G (10 mg/l), Streptomycin (10 mg/l), and Gentamicin (10 mg/l) for 5 days before recording. Sodium currents in oocytes were examined by two-electrode voltage clamp as described by Krafte et al., cited elsewhere herein, which disclosure is hereby incorporated by reference. The voltage and electrodes were filled with 1% agarose in 1M KCl and had resistance between 0.1 to 1 ohm. Bath solution contains 96 mM NaCl, 1.8 mM $CaCl_2$, 2.0 mM KCl, 1.0 mM $MgCl_2$, and 5.0 mM HEPES pH7.5. Leak subtraction was done by on-line P/4 procedure (Bezanilla and Armstrong, 1977, J. Gen. Physiol., vol. 70, 549–566, which disclosure is hereby incorporated by reference).

EXAMPLE II

CYTOGENETIC LOCALIZATION OF tipE

As a prelude to molecular cloning of tipE gene, the tipE locus, which had been mapped by recombination to chromosome 3 at 13.5±0.4 (Jackson et al., 1986, cited elsewhere herein, which disclosure is hereby incorporated by reference), was cytogeneticly analyzed. Three new chromosome aberrations have been isolated by their failure to complement tipE paralysis. These new chromosome aberrations along with other deficiencies in this region have localized the tipE gene to salivary gland chromosome band 64B2. One of the new alleles, T(2;3)TE2 is a translocation between chromosome 2 and 3. The localization of the second chromosome translocation breakpoint by chromosome walking led to the isolation of a 7.4 kb genomic fragment which rescues tipE paralysis as shown by germline transformation. Three transcripts encoded by this 7.4 kb genomic DNA were identified and their expression patterns were determined. These results lay the background for determining the nature of the tipE gene product by molecular cloning.

EXAMPLE III

ISOLATION OF NEW tipE ALLELES

Prior to this study the only cytogenetic information about tipE mutation was the mapping to position 13.5 on chromosome 3 by recombination (Kulkarni and Padhye, 1982, cited elsewhere herein, which disclosure is hereby incorporated by reference). To precisely localize and facilitate cloning of tipE gene three γ-ray induced chromosome rearrangements that fail to complement tipE were isolated. Complementation testing results of these rearrangements with tipE are presented in Table 1. Df(3L)TE1 (abbreviated as TE1) is a deficiency with visible breakpoints at 64A1-5 and 64B12-14. T(2;3)TE2 (abbreviated as TE2) is a reciprocal translocation between chromosomes 2 and 3 with breakpoints at 26A3 and 64B2. Df(3)TE3 (abbreviated as TE3)

TABLE 1

| Complementation testing of new tipE alleles | | | | |
|---|---|---|---|---|
| | TE1 | TE2 | TE3 | tipE |
| TE7 | lethal | | | |
| TE2 | ts | lethal | | |
| TE3 | lethal | ts | ND | |
| tipE | ts | ts | ts | ts | ts = temperature sensitive paralysis at 38°
ND = not done
lethal = no adults eclosed; stage of lethality not determined is a deficiency with breakpoints at 64A6 and 64B12-14. TE1 and TE2 are homozygous lethal. However, the TE1/TE2 double heterozygotes are viable and show temperature-induced paralytic phenotype. This suggests that the lethality in TE2 is not associated with the 64B2 breakpoint which affects LipE gene. TE3 behaves genetically as though linked to a T(Y;3) translocation. The breakpoint on TE3 involved in the T(Y;3) translocation has not yet been determined.

EXAMPLE IV

CYTOLOGICAL LOCALIZATION OF tipE

Figure 1:
FIG. 1 summarizes the cytogenetic map of tipE and other markers in the 64AB region. The black bars represent deletions with breakpoint uncertainties indicated by hatched regions. The right-most column are the results of complementation testing of the chromosome aberration over tipE (ts=temperature sensitive paralysis). The localization of cloned Gad, ras2, src1 and AChR, indicated at the bottom of the figure, was determined directly by in situ hybridization of the clones to polytene chromosomes from individuals heterozygous for the various aberrations. The open breaks indicate deletions that extend beyond the limits of the chromosome diagram shown at the top of the figure. References are to Wohlwill and Bonner, 1991, Genetics, vol., 128, 763–775; M. Simon; Lindsley and Zimm, 1992, The Genome of Drosophila melanogaster, Academic Press, San Diego; and R. Rawson.

Besides the newly isolated TE1, TE2 and TE3 chromosome aberrations, six other deficiencies were isolated in this region by others during the course of our studies. They are: Df(3L)HR277 with breakpoints at 63B6; 64B12 and Df(3L) HR298 with breakpoints at 63B1; 64A6 (WOHLWILL and BONNER 1991), Df(3L)ems[13] with breakpoints at 64B2-4; 64E, Df (3L)x[37] with breakpoints at 63E6-9; 64B14-17 (Lindsley and Zimm, 1992, cited elsewhere herein, which disclosure is hereby incorporated by reference), Df(3L) GN19 with breakpoints at 63E6-9; 64B2-4 and Df(3L)GN34 with breakpoints at 63E9-F7; 64A7-B2. FIG. 1 summarizes complementation testing of these deficiencies over tipE. Deficiencies HR277, X[37] and GN19 uncover tipE but deficiencies HR298, ems[13] and GN34 do not. Using these results, the tipE locus was localized at 62B2.

EXAMPLE V

MAPPING OF CLONED GENES IN 64AB REGION

A number of neurologically interesting genes were cloned from the 64AB region including: glutamic acid decarboxylase (Gad, Jackson et al., 1990, J. Neurochem., vol. 54, 1068–1078, which disclosure is hereby incorporated by reference), oncogene homologue Ras2 (Neuman-Silberberg et al., 1984, Cell, vol. 37, 1027–1033; Mozer et al., 1985, Mol. Cell Biol., vol. 5, 885–889, which disclosures are hereby incorporated by reference) and Src1 (Hoffman-Falk, et al., 1983, Cell, vol. 32, 589–598, which disclosure is hereby incorporated by reference) and a nicotinic acetylcholine receptor subunit (Acr64B, Hermans-Borgmeyer et al., 1986, EMBO J., vol. 5, 1503–1508; Wadsworth, 1988, Mol. Cell Biol., vol. 8, 778–785, which disclosures are hereby incorporated by reference). These genes were ordered with respect to the rearrangement breakpoints. The gene closest to tipE as defined by the TE2 breakpoint served as the starting point of chromosome walking. In situ hybridization to polytene chromosomes showed that the Gad gene is uncovered by HR298 and TE1 but lies distal to TE3. Therefore, the Gad gene localizes between the distal breakpoint of TE1 and the distal breakpoint of TE3 in 64A1-5. The Src1 gene is proximal to the TE1, TE3 and HR277 deficiencies, i.e. it is proximal to 64B12. The Ras2 and Acr64B genes are both uncovered by TE1, TE3 and HR277. Neither gene is uncovered by HR298. The Ras2 clone hybridizes distal to the TE2 breakpoint whereas Acr64B is proximal to TE2. These results, summarized in FIG. 1, not only provided a starting point for the localization of TE2 translocation breakpoint on chromosome 3 by chromosome walking, but also provided very useful information for screening mutations involving the aforementioned genes. One example is the subsequent successful use of TE1 and TE3 in the screening for Gad mutations (Kulkarni et al., 1994, Mol. Gen. Genet., vol. 243, 555–564, which disclosure is hereby incorporated by reference).

EXAMPLE VI

LOCALIZATION OF TE2 BREAKPOINT BY CHROMOSOME WALKING

Figure 2:
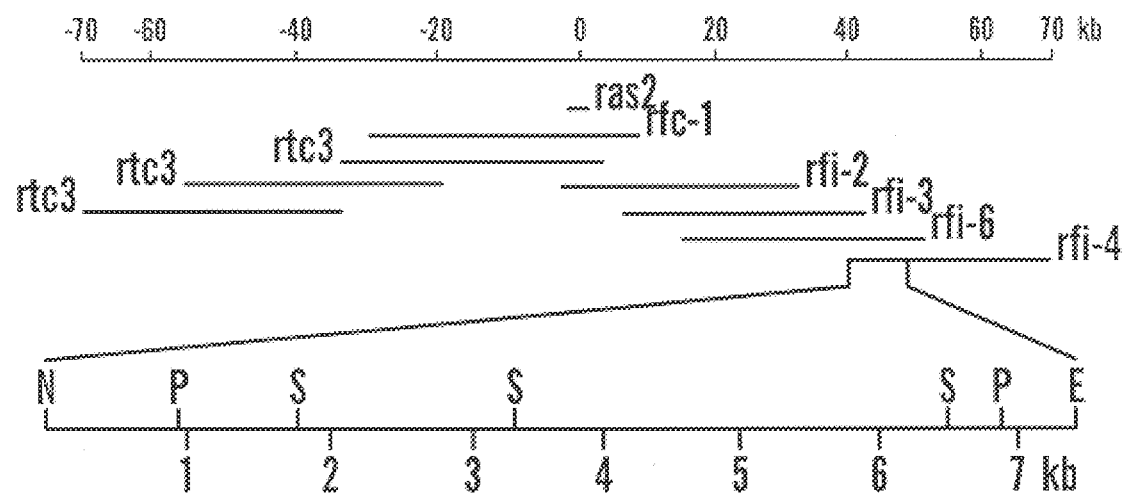
FIG. 2 is a summary of the chromosome walk. The abbreviations for restriction enzymes are: E=EcoRI, N=NotI, P=PstI, S=SacI.
Figure 3:
FIG. 3 is a photomicrograph illustrating the in situ hybridization of cosmid clone rfi-4 to polytene chromosomes from TE2/+ heterozygotes. The arrows show the hybridization signal of rfi-4 clone crossing the translocation breakpoint.

Since the TE2 translocation disrupts tipE gene, it provides the best localization of tipE gene. A chromosome walk was initiated from the Ras2 gene to localize the TE2 translocation breakpoint. A total of 140 kb genomic DNA was isolated by screening the cosmid library depicted in FIG. 2. In situ hybridization to TE2/+ polytene chromosomes showed that cosmid clone rfi-4 crossed the translocation breakpoint, as shown in FIG. 3. To confirm this, various fragments of the insert from this cosmid clone were used to probe genomic Southern blots made from +/+, TE2/+ and TE2/TE1 flies for altered restriction fragments. A 7.4 kb Not I/EcoRI fragment of the cosmid clone identifies altered EcoRI, SacI and PstI restriction fragments, indicating that the TE2 translocation breakpoint falls within this 7.4 kb fragment.

EXAMPLE VII

EFFECT OF TE2 TRANSLOCATION

Figure 4:
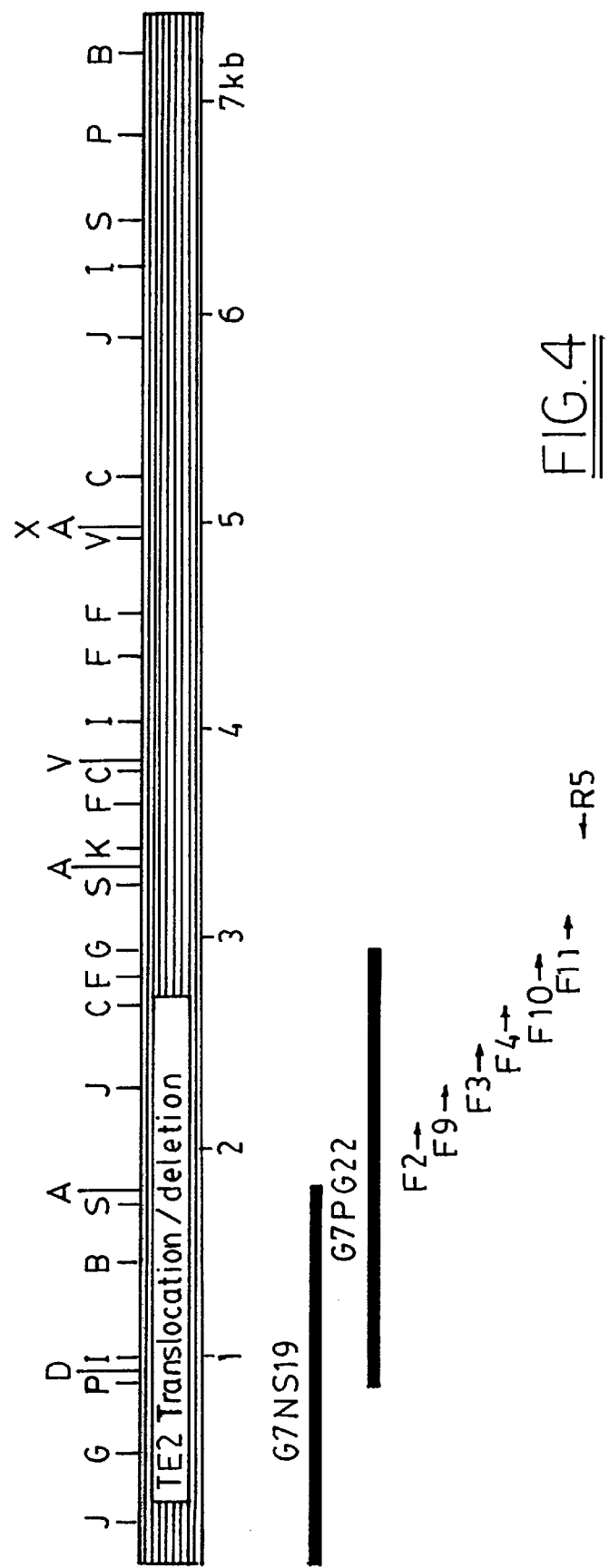
FIG. 4 is an illustration of the restriction map of the 7.4 kb genomic DNA fragment which crosses the TE2 translocation breakpoint. Locations of two probes (G7NS19 and G7PG22) used in the genomic Southern blots (FIG. 4B) and primers (F2, F3, F4, F9, F10, F11, F12 and R5) used in PCR (FIG. 4C) are indicated. The abbreviations used for restriction enzymes are: A=AvaI, B=BstXI, C=ClaI, D=ApaI, E=EcoRI, F=AccI, G=BglI, I=BstEII, J=HincII, K=KpnI, N=NotI, P=PstI, S=SacI, V=EcoRV and X=XhoI.

Genomic Southern blot analysis was simplified by using strains carrying the TE2 translocation over the deletion TE1 since the deletion removes all DNA in the area of the translocation. Genomic Southern blots digested with PstI and SacI revealed that two restriction fragments disappeared from TE1/TE2 genomic DNA, indicating that both PstI and SacI sites were altered. This result suggested that there might be a deletion associated with the translocation. In the event of simple translocation, for a given enzyme the size of one restriction enzyme fragment might change but should be replaced by two different sized fragments. In contrast, in the case of deletion associated with the translocation, many restriction enzyme fragments would be altered simultaneously. To test this, the 7.4 kb genomic fragment was subjected to detailed restriction enzyme digestion, as summarized in FIG. 4. Various pieces from this fragment were used to probe genomic Southern blots from +/+ and TE2/+ and TE2/TE1 genomic DNA digested with various restriction enzymes. Two restriction fragments disappeared from TE2/TE1 when genomic DNA was digested with either BglI, PstI, ApaI, SacI or AvaI, suggesting the deletion of all of these sites. In each restriction digestion, only one new fragment appears instead of two in the TE1/TE2. This is because the probes used (FIG. 4A, heavy bars) did not cross the whole deletion region. Thus, only the part of each probe which lies outside the deletion would hybridize to the altered restriction fragments in TE2. This added further evidence for a deletion associated with the TE2 translocation.

To further confirm the existence of the deletion, a series of primers from the deletion region were designed based on sequence information from the 7.4 kb genomic fragment. These primers were used to amplify from wild-type and TE2/TE1 genomic DNA. Primers which fall into the deletion region, even when paired with a primer outside the deletion, would not amplify from TE2/TE1 genomic DNA although the expected products should be obtained using wild-type genomic DNA as template. The PCR results indicated that the 4 forward primers (F2, F9, F3, F4) which fall into the deletion region as defined by genomic Southern analysis failed to amplify from TE2/TE1 genomic DNA, while expected products were obtained from the wild-type genomic DNA. Forward primers falling outside the deletion (F10, F11) amplify with both TE2/TE1 and wild-type templates. These PCR results confirmed the existence of the deletion detected by genomic Southern blots and also helped to define the size of the deletion which is about 2.5 kb.

EXAMPLE VIII

EFFECT OF TE2 TRANSLOCATION/DELETION ON MULTIPLE TRANSCRIPTS

Since the TE2 translocation disrupts tipE gene, all the transcripts disrupted by TE2 translocation/deletion are candidates for tipE gene. To identify the disrupted transcripts, Northern blots were prepared using poly(A+) RNA produced from +/+ and TE2/TE1 flies. A series of genomic DNA probes, which included the TE2 translocation/deletion and flanking regions, were used to probe the blots. As illustrated in FIG. 5B, at least 7 different sized transcripts (7.0 kb, 6.0 kb, 5.4 kb, 4.4 kb, 3.4 kb, 1.7 kb and 1.0 kb) were affected by the TE2 translocation/deletion. The 7.0 kb, 6.0 kb and 1.0 kb transcripts have reduced expression levels while the other four transcripts are physically disrupted by the TE2 translocation/deletion. The original transcripts disappeared from TE2/TE1 flies, and altered size transcripts appeared in TE2/TE1. The Northern blots from wild-type flies, indicated that the 1 kb mRNA is expressed in heads, bodies and leg antennal fractions; the 7.0 kb, 5.4 kb and 4.4 kb mRNA are in both heads and leg antennal fractions; the 6.0 kb and 3.4 kb mRNA are mainly in heads while the 1.7 kb is only in bodies. Table 2 summarizes these transcripts and their expression in TE2/TE1 flies. By probing Northern blots with smaller genomic DNA fragments the positions of these mRNA relative to the TE2 translocation/deletion were roughly mapped as depicted in FIG. 5B.

The existence of multiple transcripts in TE2 translocation/deletion region complicates the identification of the tipE transcript since it is a heavily transcribed genomic region. A recent screening for recessive lethal mutations in 64AB region using TE1 and TE3 identified at least 19 essential genes (Kulkarni et al., 1994, cited elsewhere herein, which disclosure

TABLE 2

Transcripts affected by TE2 translocation/deletion

| Size | Expression pattern in wild-type | Expression in TE2/TE1 |
| --- | --- | --- |
| 7.0 kb | Head, Leg | Reduced |
| 6.0 kb | Head | Reduced |
| 5.4 kb | Head, Leg | Disrupted |
| 4.4 kb | Head, Leg | Disrupted |
| 3.4 kb | Head | Disrupted |
| 1.7 kb | Body | Disrupted |
| 1.0 kb | Head, Body, Leg | Reduced | is hereby incorporated by reference) in this region. Several of these mutations are close to the tipE locus. The transformants generated in these studies may be useful for determining which transcripts are candidates for the various lethal mutations.

EXAMPLE IX

EFFECT OF 7.4 kb GENOMIC DNA ON tipE PARALYSIS

Due to the numerous transcripts disrupted by the TE2 translocation/deletion, it was necessary to use transformation rescue (Spradling, 1986, cited elsewhere herein, which disclosure is hereby incorporated by reference) to narrow the number of candidate tipE transcripts. Germline transformation was performed with the cosmid clone rfi-6 (FIG. 2), various fragments from this cosmid clone, and the 7.4 kb genomic fragment from cosmid clone rfi-4 (FIG. 2). FIG. 5A shows those fragments which rescue the tipE paralysis as solid bars. The cross-hatched bars denote fragments which fail to rescue. Each of the rescuing fragments (40 kb, 12 kb, and 7.4 kb) includes the translocational/deletion breakpoint. These rescue results eliminate the 7.0 kb, 6.0 kb, 3.4 kb and 1.0 kb mRNA as the tipE candidate transcript since they are each transcribed from genomic DNA outside the 7.4 kb region, as can be seen by reference to FIG. 5B. The remaining 5.4 kb, 4.4 kb and 1.7 kb mRNAs are all transcribed from completely within the 7.4 kb genomic DNA. Probing Northern blots with single-stranded probes revealed that all three mRNAs are in the same orientation. All the three transcripts are extensively overlapped. Therefore it is likely that they are alternatively spliced forms from a single transcriptional unit. Since this is the only transcriptional unit detected from the 7.4 kb genomic DNA which rescue the tipE paralysis, we conclude that these transcripts are products of the tipE gene. Since the 7.4kb genomic DNA fragment completely rescues the tipE paralytic phenotype, it must contain not only the complete transcript, but also the necessary upstream regulatory regions controlling gene expression. The small size of this rescuing construct eliminates the possibility that the tipE encodes another sodium channel a subunit distinct from para and DSC1 since the $\alpha_1$ subunit is a very large protein (MW>150,000) encoded by large transcripts, generally 9–10 kb.

EXAMPLE X

ISOLATION OF cDNA CLONES

Localization of the translocation breakpoint by chromosome walking led to the isolation of a 7.4 kb genomic fragment which rescues tipE paralysis, suggesting that it contains tipE gene. Northern analysis showed that it encodes 3 different size mRNAs (5.4 kb, 4.4 kb and 1.7 kb) which are all disrupted by T(2;3)TE2 translocation. The abundant 4.4 kb and the much less abundant 5.4 kb mRNA are predominantly expressed in heads and legs while the 1.7 kb mRNA is mainly expressed in bodies. Fragments from the 7.4 kb genomic DNA were used to screen a Drosophila head cDNA library. Three cDNA clones corresponding to the 4.4 kb mRNA were isolated with the longest one has 4 kb insert. Two partial clones corresponding to the 5.4 kb mRNA were also isolated using genomic DNA probes specifically hybridize to the 5.4 kb mRNA. The cDNA clones corresponding to the 1.7 kb mRNA was obtained by reverse transcription-coupled PCR (RT-PCR) amplification of body mRNA using primers derived from the sequence of the 7.4 kb genomic DNA.

EXAMPLE XI

ANALYSIS OF cDNA SEQUENCE AND GENOMIC ORGANIZATION

Figure 6:
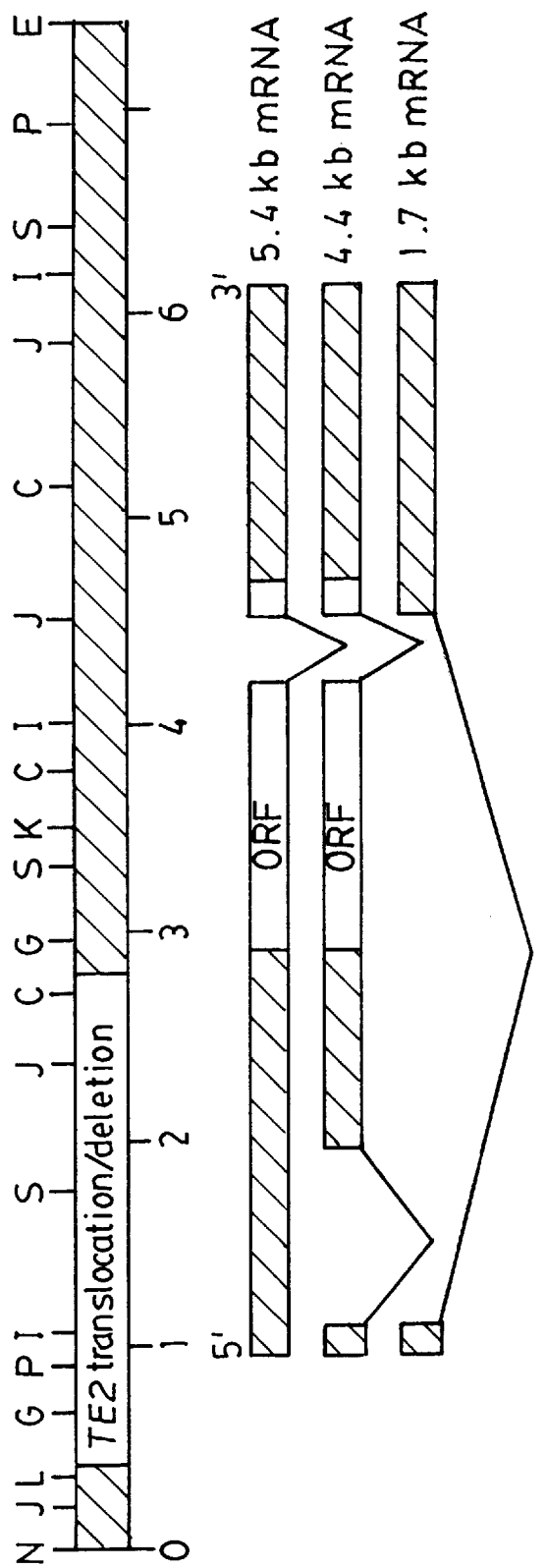
FIG. 6 illustrates a restriction map of the 7.4 kb genomic fragment which rescues tipE paralysis. The translocation breakpoint of T(2;3)TE2, which is associated with a 2.5 k deletion, is indicated. Three alternatively spliced forms of tipE mRNA are detected. Open boxes indicate the open reading frames (ORF) as revealed by sequencing the cDNA clones. Restriction sites shown are: C, ClaI; E, EcoRI; G, BglI; I, BstEII; J, HincII; K, KpnI; L, HpaI; N, NotI; P, PstI; S, SacI.

The whole 7.4 kb genomic DNA fragment and all the cDNA clones corresponding to different mRNAs were sequenced. Comparison of sequence data from the cDNA clones and the genomic fragment revealed that all the three mRNAs are alternatively spliced forms from the same transcript. The most abundant form (4.4 kb mRNA) consists of three exons. A restriction map of the 7.4 kb genomic fragment which rescues tipE paralysis is provided in FIG. 6 A Northern blot of poly(A+) RNA from heads, bodies, and legs, probed with a 4 kb cDNA clone corresponding to the 5.4, 4.4, and 1.7 kb RNA and then reprobed with rp49 indicated that the 1.7 and 4.4 kb RNA were present in the heads, bodies, and legs of flies, but that the 5.4 kb RNA was a major component of the heads and legs but not the bodies of flies. 5.4 kb mRNA is an alternatively spliced form with the intron between first and second exon not spliced. Surprisingly, the 1.7 kb mRNA is an alternative spliced form without most part of the open reading frame. Alternative long open reading frames from this splicing form were not identified. One possible explanation is that cells use splicing mechanism to inactivate the gene where tipE product is not needed.

The 4 kb cDNA clone which corresponds to the most abundant 4.4 kb mRNA contains a 5' untranslated sequence of 1045 bp, (SEQ. ID NO: 3) an open reading frame (ORF) of 1356 bp (SEQ. ID NO: 4) and a 3' untranslated region of 1549 bp (SEQ. ID NO: 5). The nucleotide sequence (SEQ. ID NO. 1) of this cDNA clone is provided in FIG. 7A. There is a poly(A) tail and 5 consensus polyadenylation sites (AATAAA) at position 2869, 3098, 3535, 3709 and 3915. The ATG at position 1046 has been designated the initial methionine. It is proceeded by 2 nearby in-frame stop codons. The 4 nucleotides immediately proceeding the initial ATG (AAAC, position 1042–1045) match very well with the consensus sequence (C/A AA A/C) for initiation of translation in Drosophila (Cavener, 1987, Nucl. Acids Res., vol. 15, 1353–1361, which disclosure is hereby incorporated by reference).

Translation of the ORF yields a protein of 452 amino acids with a calculated molecular weight of 50.2 kDa. The deduced amino acid sequence (SEQ. ID NO. 2) is presented in FIG. 7A. It is highly negatively charged with a pI of 4.17. Aspartic acid and glutamic acid consist 14% of the total amino acids. Database search revealed no significant sequence similarity to any other proteins. The deduced protein sequence has two hydrophobic domains as judged by hydropathy analysis (Kyte and Doolittle, 1982, J. Mol. Biol., vol. 157, 105–132, which disclosure is hereby incorporated by reference). The hydrophobicity plot of the tipE protein is provided in FIG. 7B. The first hydrophobic domain contains 39 amino acids (from position 14 to 52) preceded by a highly charged (8 out of 13 amino acids are charged) N-terminal sequence. Although this hydrophobic domain is at the N-terminal, it is unlikely that it functions as a signal peptide for the following reasons: (1) most eukaryotic signal peptide sequences are about 20 amino acids with the longest about 35 amino acids (von Heijne, 1985, J. Mol. Biol., vol. 184, 99–105, which disclosure is hereby incorporated by reference) while this domain would have 52 amino acids if cleaved as a signal peptide; (2) sequence analysis does not give a predictable cleavage site using the (−3,−1) rule (von Heijne, 1986, Nucl. Acids Res., vol. 14, 4683–4690, which disclosure is hereby incorporated by reference); (3) in vitro translation in the presence of microsomes suggested that the N-terminal was not cleaved (see below). For these reasons, this hydrophobic domain was designated the first transmembrane domain. The second transmembrane domain is from position 274 to 300 (27 amino acids). Other interesting features of this protein include a consensus site for potential PKC phosphorylation of threonine at N-terminal (position 9) and 5 potential N-glycosylation sites in the loop between the two transmembrane domains at position 72, 102, 108, 212 and 237.

EXAMPLE XII

EFFECT OF THE tipE MUTATION ON THE ORF

To determine the molecular nature of the mutation in tipE flies we sequenced genomic DNA of tipE mutants corresponding to the 7.4 kb fragment which rescues the paralysis. Sequencing templates were generated by PCR amplification of genomic DNA. The sequence of genomic DNA from the mutants revealed a point mutation in nucleotide position 1759 of the nucleotide sequence shown in FIG. 7A. This T→A mutation changes a cysteine (TGT) to a stop codon (TGA). This stop codon would result in a truncated protein of 237 amino acids. It would lack 36 amino acids of the loop between the two transmembrane domains, the second transmembrane domain and the C-terminal and would have a predicted molecular weight of 27 kDa.

Three approaches were used to exclude the possibility that the detected point mutation was a PCR artifact. First, the PCR product amplified from tipE genomic DNA without subcloning was sequenced directly. In this case even if an error occurred in the first round of amplification, only 25% of the final product would contain the error. Since subcloning requires to pick up single colonies, it may end up with a template containing the error. Direct sequencing PCR products would be more reliable (reviewed by Rao, 1994, Anal. Biochem., vol. 216, 1–14, which disclosure is hereby incorporated by reference). Second, both Taq and Pfu (a high fidelity DNA polymerase) were used for PCR and exactly same results were obtained. Third, the mutation was found to have also eliminated a RsaI site (GTAC to GAAC). Digestion of PCR products amplified from mutant flies showed that the RsaI site was missing from all the PCR product.

EXAMPLE XIII

EFFECT OF tipE GENE EXPRESSION ON PUPAL DEVELOPMENT

To confirm that the protein predicted from the cDNA clone is the tipE gene product we did germline transformation with ORFs of both the wild-type and mutant cDNA. cDNA fragments were constructed into a transformation vector containing a heat shock promoter (pCaSpeR-hs, Thummel and Pirrotta, 1992, cited elsewhere herein, which disclosure is hereby incorporated by reference) and injected into w;tipE se homozygous embryos. Homozygous transformant flies (two copies of cDNA in w;tipE se background) were used. To induce the gene expression, transformant flies were heat-shocked at 35° C. for 1 hour. Surprisingly, heat shock of adult transformant flies containing wild-type cDNA failed to rescue the paralysis phenotype. Continuation of the heat shock process (once a day) for up to two weeks still did not rescue the paralysis.

Figure 8A:
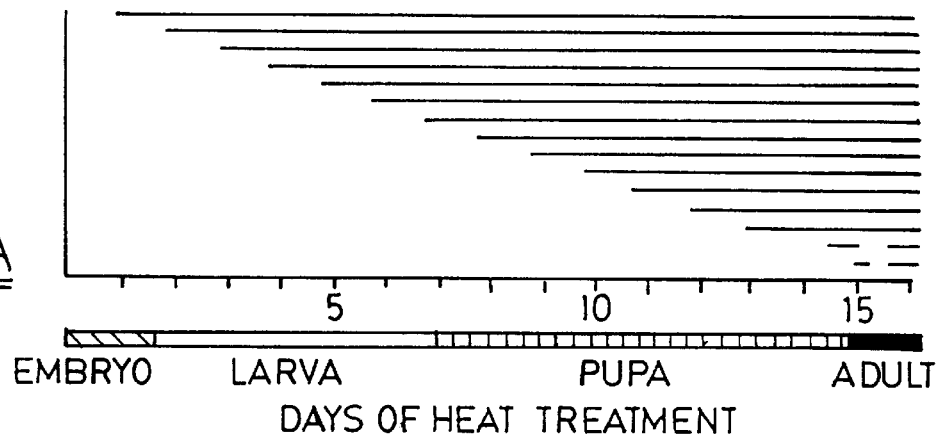
FIGS. 8A and 8B respectively illustrate the results of the shift-up and shift-down heat shock experiments on homozygotes tipE flies transformed with tipE+ cDNA under the control of a heat shock promoter.
Figure 8B:
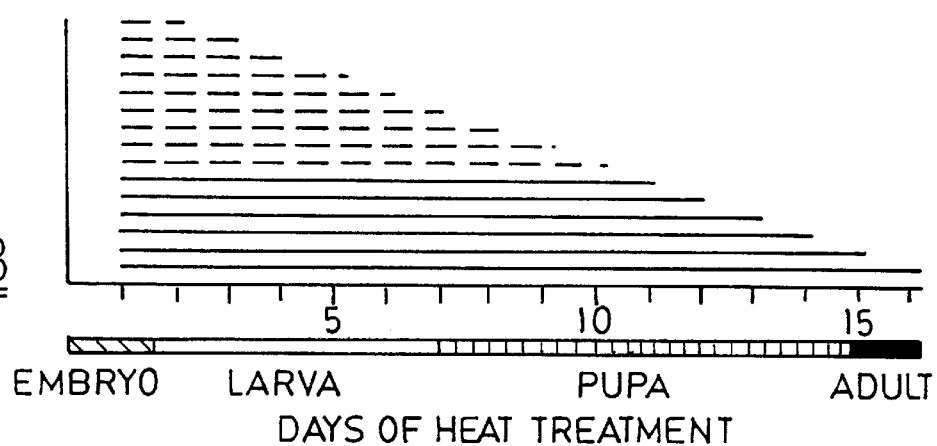

To test the possibility that tipE protein might be needed during development, the 1 hour heat shock was performed once a day throughout the development stages until eclosion. Interestingly, the eclosed transformants with wild-type cDNA no longer exhibited temperature-induced paralysis anymore. Moreover, no further heat shock was required after eclosion. That is, the paralysis phenotype is permanently "cured" by the induction of tipE gene expression during development. As a control, transformants with tipE mutant cDNA failed to rescue the paralysis. The above results prompted a further investigation to ascertain the developmental period when tipE protein is required in order to rescue the adult paralysis. The tipE gene expression was induced by heat shocking the transformants at different developmental stages using a strategy similar to the "shift-up" and "shift-down" experiments of Suzuki, 1970, Science, vol. 170, 695–706, which disclosure is hereby incorporated by reference. In the "shift-up" experiment, heat shocks were started at different times of development and continued once a day until eclosion (FIG. 8A). This would determine the latest time during development when the start of tipE gene expression is still able to rescue the adult paralysis. In the "shift-down" experiment, heat shocks were started 24 hours after egg laying for all the eggs and continued. Every 24 hour a group of eggs (or larvae or pupae later on as they developed) were removed from treated group (FIG. 8B).

Figure 8C:
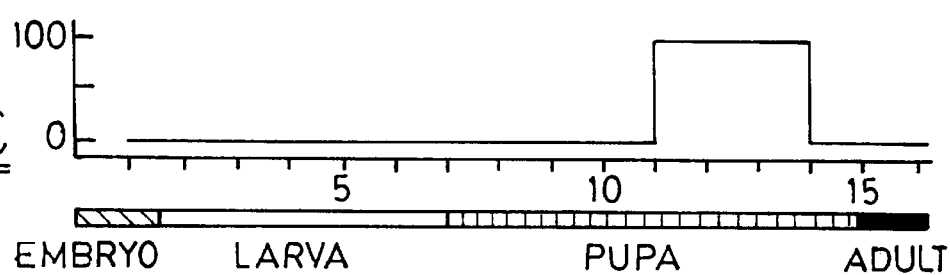
FIG. 8C illustrates the critical phase when tipE+ is required to prevent adult paralysis, as deduced from the shift-up and shift-down experiments.

This would determine the earliest time during development when stopping expression of tipE gene would not affect the rescue of the adult paralysis. The combination of the "shift-up" and "shift-down" experiments would define a developmental window during which the expression of tipE gene is essential in order to rescue the adult paralysis (FIG. 8C). All the flies heat shocked for the different periods during development were tested for temperature-induced paralysis after their eclosion. As shown in FIG. 8, starting heat shock as late as 48 hours before eclosion (71% of pupal development) is sufficient to rescue the adult paralysis. The "shift-down" experiment showed that in order to rescue the paralysis tipE gene must be expressed beyond 72 hours post puparium formation (43% of pupal development). These results suggest that in order to rescue the adult paralysis tipE gene must be expressed during the period from 72 to 144 hours following puparium formation (43%–86% pupal development, critical phase, illustrated in FIG. 8C). A single heat shock at anytime during the critical phase failed to completely rescue the paralysis, suggesting that a period of tipE gene expression during development is required.

EXAMPLE XIV

EFFECT OF OVEREXPRESSION OF tipE ON HEAT INDUCED LETHALITY

Figure 9:
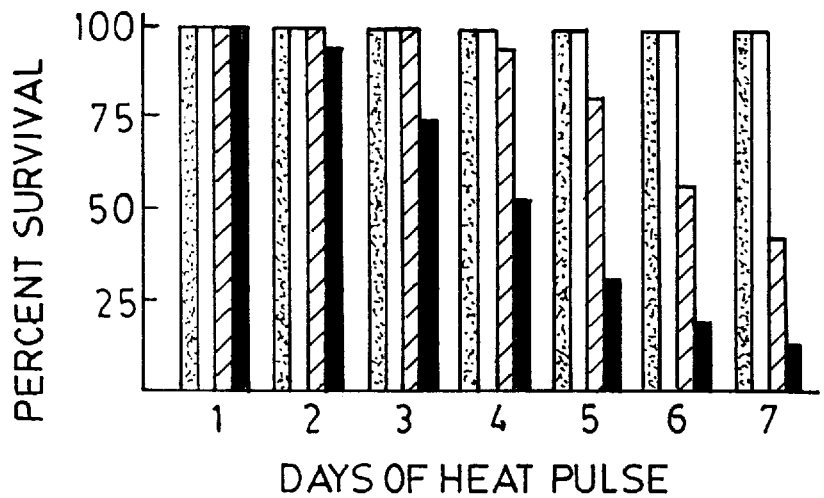
FIG. 9 illustrates the rescue of heat-induced adult lethality in tipE cDNA mutants (black bars), wild-type flies (gray bars), tipE mutant with wild-type transgene (open bars), and tipE mutant with mutant transgene (striped bars).

Example XIII, above, demonstrated that repeated heat shock (35° C., 1 hour/day) of adult LipE$^+$ cDNA transformant flies failed to rescue the paralysis phenotype. During these heat shock experiments, tipE mutant flies were observed to gradually die as the heat shock continued everyday (heat-induced lethality) while the tipE$^+$ cDNA transformant flies survived as well as wild-type flies. These observations are graphically illustrated in FIG. 9. Although induction of the tipE$_+$ gene expression in middle to late pupae stage is enough to permanently rescue the paralysis, this result indicates that tipE protein plays a role in protecting the adult nervous system against lethal heat stress.

Transformant flies with tipE mutant cDNA in w;tipE se background were also tested. Although these transformant flies did not rescue paralysis even when heat shocked during development, they exhibited much lower heat-induced lethality compared to the tipE flies when repeatedly heat shocked as adults. That overexpression of the truncated protein partially rescues heat-induced lethality in tipE flies, suggests a residual function for the truncated tipE protein.

EXAMPLE XV

TEMPORAL AND SPATIAL LOCALIZATION OF tipE GENE EXPRESSION

To determine where the tipE gene is expressed, a digoxigenin-labeled antisense DNA probe was used on whole mounts of 16–18 hour embryos. tipE$^+$ mRNA was found to preferntially express in the nervous system.

Figure 10:
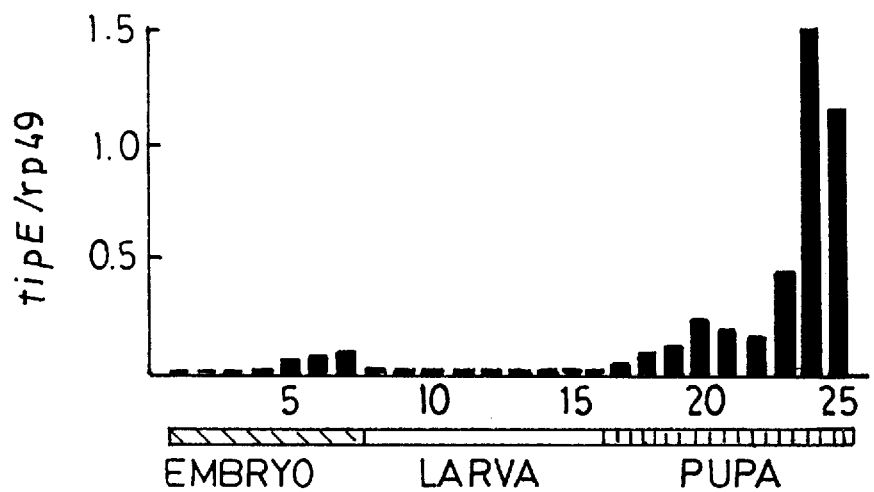
FIG. 10 is a histogram corresponding to the temporal distribution of tipE gene expression during development of wild-type $Drosophila$ $melanogaster$. Wild-type samples were collected and staged at 25° C. Ten μg of poly(A+) RNA was loaded per lane. Blots were probed with the same cDNA fragment used in transformation rescue and reprobed with rp49 to standardize for mRNA recovery and loading differences. Signals on blots were quantitated using a Betascope blot analyzer (Betagen).

The temporal distribution of the tipE transcripts was analyzed quantitatively using Northern blots of mRNA prepared from different stages of flies. To standardize for mRNA recovery and loading differences, the blots were reprobed with a cDNA clone encoding a ribosomal protein, rp49, which is expressed widely (O'Connell and Rosbash, 1984, cited elsewhere herein, which disclosure is hereby incorporated by reference). FIG. 10 shows the quantitation of the 4.4 kb tipE mRNA relative to rp49 mRNA levels in different developmental stages. There is a small peak expression in middle to late embryonic stage (13–21 hours post-oviposition, 62%–100% embryonic development, lane 5–7). The expression is dramatically increased in the pupae stage, especially in middle to late pupae (44%–100% of pupal development, lane 20–25). The high expression level in the middle to late pupae stages matches the critical phase defined by the transformation rescue using the cDNA clone.

EXAMPLE XVI

MEMBRANE TOPOLOGY OF tipE PROTEIN

Figure 11:
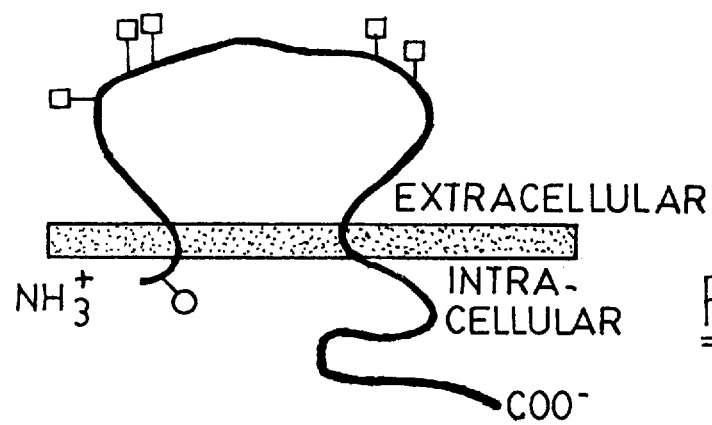
FIG. 11 illustrates the predicted membrane topology of tipE protein. The open circle indicates a consensus protein kinase C phosphorylation site. The open squares show the consensus sites for N-glycosylation.

Hydropathy analysis of deduced tipE protein predicted two hydrophobic domains long enough to span plasma membranes, suggesting that tipE is a transmembrane protein. To confirm this in vitro translation was performed in the presence of microsomes which allow in vitro translated membrane proteins be correctly translocated, glycosylated and signal peptide cleaved (Blobel and Dobberstein, 1975, J. Cell. Biol., vol. 67, 852–862; Yost et al., 1983, Cell, vol. 34, 759–766; Audigier et al., 1987, Proc. Nat. Acad. Sci. USA, vol. 84, 5783–5787, which disclosures are hereby incorporated by reference). After in vitro translation, the microsomes were treated at high pH (0.1M NaCO$_3$, pH11.5). This treatment disrupts microsomes and extracts vesicle contents as well as peripheral membrane proteins, but not integrated membrane proteins (Fujiki et al., 1982,22 J. Cell. Biol., vol. 93, 97–102; Gilmore and Blobel, 1985, Cell, vol. 42, 497–505, which disclosure is hereby incorporated by reference). Treatment of microsomes at high pH did not remove tipE protein from microsomes, strongly suggesting that tipE protein is an membrane-integrated protein. The results also showed that the molecular weight of the in vitro translated tipE protein in the presence of microsomes (70 kDa,) is much higher than that without microsomes (50 kDa,). This increase of size is due to extensive glycosylation of tipE protein since treatment of the sample with endoglycosydase reduced the size back to the predicted 50 kDa. FIG. 11 depicts the predicted membrane topology of tipE protein. There are 5 potential N-glycosylation sites in the loop between the two transmembrane domains. Since N-glycosylation occurs on the luminal side of the microsomal membrane, good evidence exists that the loop is translocated into the lumen of microsomes and, therefore, extracellular in cells.

To confirm the prediction that the first hydrophobic domain is not a signal peptide the same in vitro translation experiment was conducted using the tipE mutant cDNA which expresses a truncated protein lacking 36 amino acids of the loop, the second transmembrane domain and the whole C-terminal.

This truncated protein has a predicted molecular weight of 27 kDa. If the first hydrophobic domain is a signal peptide, it would be cleaved along with the N-terminal fragment when translated in the presence of microsomes. The cleavage would reduce the protein size by 6 kDa (52 amino acids). The cleaved protein would be secreted into the lumen of microsomes and washed off the microsomes at high pH because it would not have a transmembrane domain. The truncated protein is still a membrane-integrated protein since treatment at high pH did not remove the protein from microsomes and there is no size reduction when translated in the presence of microsomes 1). These results strongly suggest that the first hydrophobic domain is a transmembrane domain.

The topology of membrane proteins can be predicted based on their signal peptides and transmembrane domains. Without a signal peptide, the predicted topology of tipE protein would put both N-terminal and C-terminal intracellularly, as shown in FIG. 11, with the first transmembrane domain serving as the start-transfer signal and the second transmembrane domain as the stop-transfer signal (Rapoport, 1985, FEBS Lett., vol. 187, 1–10; Wickner and Lodish, 1985, Science, vol. 239, 400–407, which disclosures are hereby incorporated by reference). To test this in vitro translation product was treated with trypsin. If a fragment of the protein is translocated cross the microsomal membrane into the lumen (and therefore is quivalent to extracellular domains in cells), it would be protected from being digested by trypsin. On the other hand, fragments outside microsomes (intracellular in cells) would be digested by trypsin. Trypsin treatment reduced the size of in vitro translated protein by about 17 kDa (from 50 kDa to 33 kDa, lane 5) which is consistent with the prediction that the C-terminal (16 kDa+1 kDa N-terminal) is on the outside of the microsomes (hence equivalent to an intracellular domain) and susceptible to trypsin digestion. The size of the fragment protected from trypsin digestion by microsomal membrane (33 kDa) is consistent with the prediction that the loop between the two transmembrane domains is extracellular (28 kDa of loop, plus 5 kDa of the two transmembrane domains). Similar results were obtained when the tipE mutant form was tested. The truncated loop is still translocated into the lumen of microsomes as indicated by heavy glycosylation and protection from trypsin digestion. These results support the prediction that tipE is a membrane protein with two transmembrane domains and both N and C-terminal are intracellular as illustrated in FIG. 11.

EXAMPLE XVII

ROLE OF tipE PROTEIN IN para SODIUM CHANNEL FUNCTION

The cloning of tipE gene made it possible to directly study the functional interaction between tipE protein and para sodium channels. Although para gene was cloned several years ago (Loughney et al., 1989, cited elsewhere herein, which disclosure is hereby incorporated by reference), it had never been functionally expressed in any expression system. With the idea in mind that tipE protein may directly modulate para sodium channel function, in vitro transcribed tipE$^+$ and para$^+$ RNA were co-injected into *Xenopus oocytes* and sodium currents were measured by two-microelectrode voltage clamp.

Figure 12B:
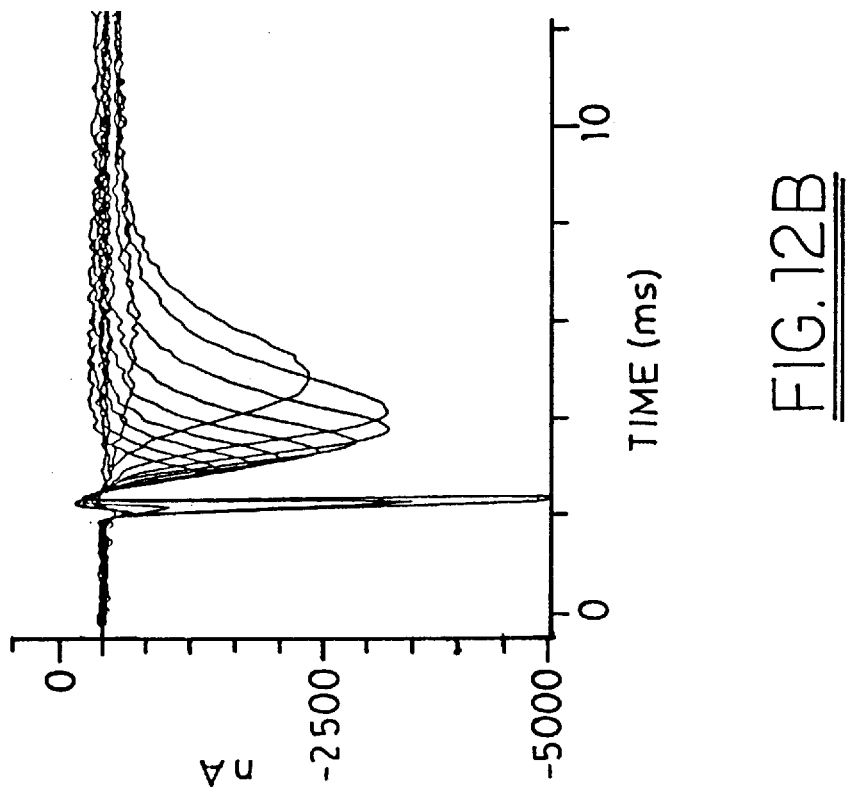
FIGS. 12A and 12B are plots of current vs time for the product of coexpression of tipE+ and para+ RNA in Xenopus oocytes. Oocytes were co-injected with either para+ and antisense tipE+ RNA (A) or para+ and sense tipE+ RNA (B). The currents shown were elicited by 20 ms voltage steps from a holding potential of −100 mV. The test potentials ranged from −50 mV to +60 mV in steps of 10 mV increments. The transient capacitive currents have been blanked.
Figure 12A:
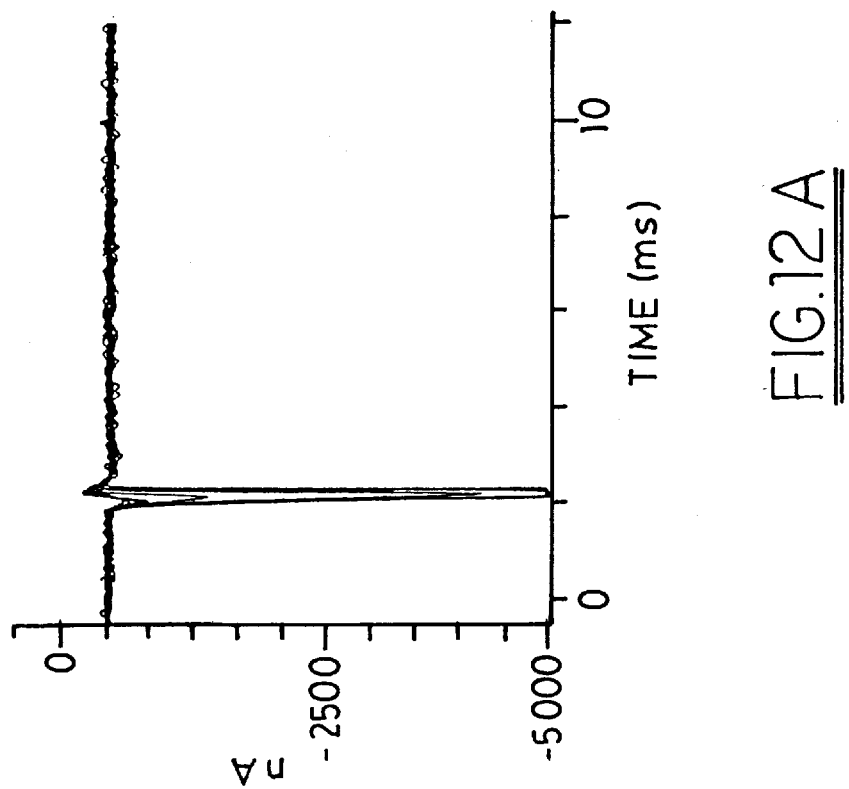
Figure 12:
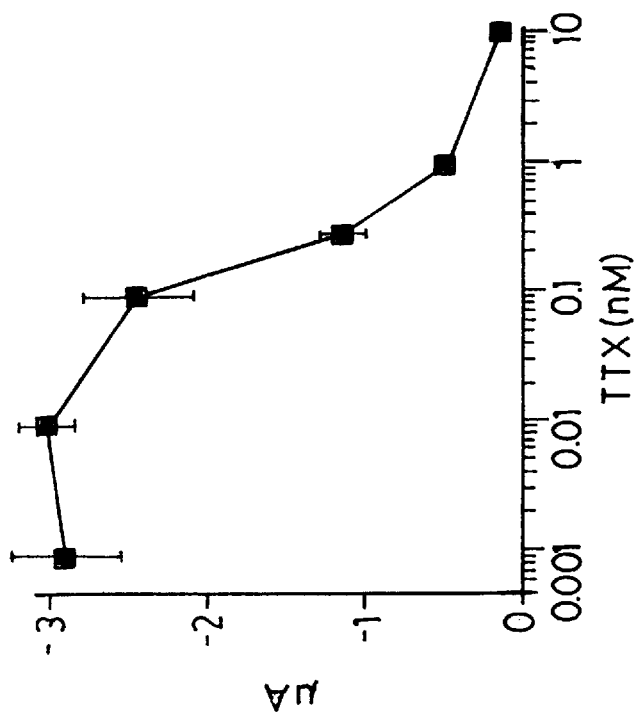
FIG. 12C is a plot of the peak inward current versus test potential (I–V curve) from average data of 11 oocytes.
FIG. 12D illustrates the TTX sensitivity of the expressed sodium channels. TTX was applied to the bath and incubated for 5 min before recording. Peak currents from five oocytes were used for each TTX concentration. Error bars show standard error of the mean.
Figure 12C:
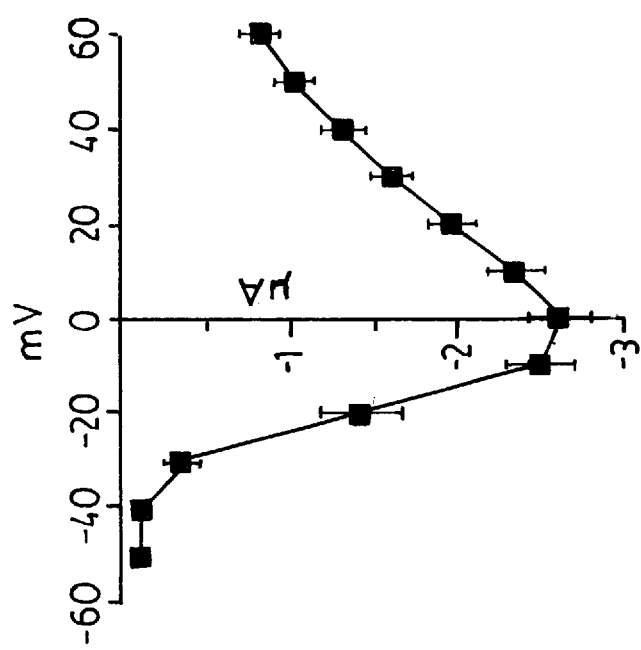

Although injection of tipE$^+$ RNA itself did not express any current in *Xenopus oocytes*, the functional expression of para sodium channel in *Xenopus oocytes* required the co-injection of tipE$^+$ RNA. As shown in FIG. 12A, sodium currents in oocytes injected with para$^+$ and anti-sense tipE$^+$ RNA were not detectable. In contrast, as shown in FIG. 12B, oocytes injected with para$^+$ and sense tipE$^+$ RNA expressed voltage-activated sodium current. The current-voltage relation of expressed para/tipE is presented in FIG. 12C. Inward current first appears at −40 to −30 mV and the peak current was observed at 0 mV. The voltage dependence (current-voltage relation) of expressed para/tipE sodium currents is comparable with that recorded from cultured Drosophila embryonic neurons (O'Dowd and Aldrich, 1988, cited elsewhere herein, which disclosure is hereby incorporated by reference). Drosophila neuronal sodium channels are highly sensitive to Tetrodotoxin (TTX), a sodium channel-specific blocker (O'Dowd and Aldrich, 1988, cited elsewhere herein, which disclosure is hereby incorporated by reference). As shown in FIG. 12D, the expressed para/tipE sodium channels are also very sensitive to TTX with an IC$_{50}$ (concentration which causes 50% inhibition) of 0.2 nM. At 10 nM, TTX completely blocks the sodium current, which is consistent with the results from cultured Drosophila embryonic neurons (O'Dowd and Aldrich, 1988, cited elsewhere herein, which disclosure is hereby incorporated by reference).

RESULTS

1. Role of tipE Gene in Functional Development of Nervous System:

The transformation rescue results, detailed above, provided new insight about the in vivo roles of tipE gene in the nervous system. Using heat shock promoter to control tipE$^+$ gene expression, tipE$^+$ gene product was shown to be required during middle to late pupae stage in order to rescue adult paralysis. Repeated induction of tipE$^+$ gene expression only in adult flies failed to rescue the paralysis. These results strongly suggest that tipE gene play an important role in the development of the nervous system during middle to late pupal stage when newly re-modeled adult nervous system undergoes maturation (Truman et al., 1993, Formation of the Adult Nervous System, pp. 1245–1275 in The Development of *Drosophila melanogaster*, edited by M. Bates and M. Arias, Cold Spring Harbor Laboratory Press, New York, which disclosure is hereby incorporated by reference). Moreover, the rescue achieved by supplying tipE$^+$ gene product during pupae stage is permanent, i.e. no further tipE$^+$ gene expression is required after eclosion, suggesting that there might be developmental defects of function and/or structure in the adult nervous system caused by the lack of tipE protein during development. These defects can only be corrected by providing normal tipE function during development. Once these defects are corrected, the flies no longer have temperature-sensitive paralytic phenotype even without continued expression of tipE$^+$ gene. It may be argued that the tipE protein might be extremely stable (virtually no turnover), such that no further expression is needed after rescue. If this is the case, then the induction of tipE gene expression at early pupae stage would also have rescued the paralysis.

The functioning of the nervous system depends on the precise patterns of neuronal connectivity. The development of these precise patterns involves pathfinding, target selection and functional connection which are accomplished by the combination of two different mechanisms as reviewed by Goodman and Shatz, 1993, Cell, vol. 72(suppl.), 77–98, which disclosure is hereby incorporated by reference: those which require neuronal activity (activity-dependent) and those which do not (activity-independent). The process of pathfinding and target selection usually occurs before neurons become active and therefore is activity-independent, while the refinement and remodeling of these coarse patterns of synaptic connection into functional connection typically rely on neuronal activity. Studies from the vertebrate visual system showed that TTX can prevent the formation of fine-grained retinotectal map without disrupting the axon growth and coarse connections (Meyer, 1982, Science, vol. 218, 589–591; Meyer, 1983, Dev. Brain Res., vol. 6, 293–298; Schmidt and Edwards, 1983, Brain Res., vol. 209, 29–39; Fawcett and O'Leary, 1985, Trends Neurosci., vol. 8, 201–206; Kobayashi et al., 1990, Dev. Brain Res., vol. 57, 29–35, which disclosures are hereby incorporated by reference). Recent studies showed that electrical activity is required for neuronal induction of transmitter receptor expression during synaptogenesis at embryonic neuromuscular junction of Drosophila (Broadie and Bate, 1993, Neuron, vol. 11, 607–619, which disclosure is hereby incorporated by reference). Using small-patch mosaics, Burg et al., 1993, J. Neurobiol., vol. 24, 803–823, which disclosure is hereby incorporated by reference, were able to study the activity-dependent development of sensory neurons in para/nap double mutants which are lethal at all temperatures. Although sensory cells in these double mutants are nonfunctional at all temperatures, their ultrastructure is normal. The branch pattern and terminal arborization of central projections of these nonfunctional sensory cells are also normal. These findings suggest that electrical activity may not be involved in pathfinding and ramification of terminal arborization, but rather may be required for establishing and maintaining its functional connectivity. Since tipE is essential for the function of para sodium channel, it is possible that similar defects of functional connectivity in the nervous system might occur in tipE mutants.

2. Function of tipE Protein:

Both ligand binding and genetic studies suggest a defect of sodium channel function in tipE mutants (Jackson et al., 1986, cited elsewhere herein; Ganetzky, 1986, cited elsewhere herein, which disclosures are hereby incorporated by reference). The sequence data presented herein clearly show that tipE is not another homologue of voltage-gated sodium channel α-subunit (usually>150 kDa). Using Xenopus oocytes expression system, tipE protein was shown to be required for the function of para sodium channel. Expression of para sodium channel in Xenopus oocytes is undetectable without the co-injection of tipE RNA. These results, along with the fact that tipE is a membrane protein, suggest that tipE may be a subunit of the para sodium channel complex essential for its function.

The para sodium channel has a high sequence homology to rat brain sodium channel α-subunits (Loughney et al., 1989, cited elsewhere herein, which disclosure is hereby incorporated by reference). Besides α-subunits, rat brain sodium channel complex contains two small auxiliary subunits, a 30 kDa $\beta_1$ and a 33 kDa $\beta_2$ (reviewed by Catterall, 1992, cited elsewhere herein; Isom et al., 1994, cited elsewhere herein, which disclosure is hereby incorporated by reference). Although some type of sodium channel α-subunits alone are sufficient to form functional channels when expressed in Xenopus oocytes, their properties are not normal. Inactivation is slower and voltage dependence is shifted to more positive membrane potential compared to the channels in intact neurons. Coexpression of α-subunits with low molecular weight RNA from rat brain (presumably containing $\beta_1$ and $\beta_2$ subunits) not only corrected the abnormality, but also dramatically increased the level of expressed sodium current (Auld et al., 1988, cited elsewhere herein; Krafte et al., 1988, cited elsewhere herein; Krafte et al., 1990, cited elsewhere herein, which disclosures are hereby incorporated by reference). Similar results were obtained when cloned 31 subunit was coexpressed with rat brain α-subunit (Isom et al., 1992, cited elsewhere herein, which disclosure is hereby incorporated by reference). These results demonstrated the importance of auxiliary subunits in the function of sodium channels. Nothing is known about the subunit constitution of Drosophila sodium channels. The tipE gene does not have sequence similarity to either $\beta_1$ (Isom et al., 1992, cited elsewhere herein, which disclosure is hereby incorporated by reference) or $\beta_2$ (Catterall, personal communication). The lack of sequence similarity to the known sodium channel small subunits could mean the identification of a new class of subunit which may form specific association with distinct α-subunit subtypes. It could also mean that tipE is a species specific subunit for sodium channels in Drosophila. However, preliminary results indicate that there are tipE homologues in rat and rabbit brains. Therefore, the cloning of tipE gene may add more diversity to the structure, function and regulation of sodium channels.

Genetic studies showed that tipE and para interact in an allele-specific way which is not correlated to the residual activities of para sodium channels in these alleles (Ganetzky, 1986, cited elsewhere herein, which disclosure is hereby incorporated by reference). The simplest explanation is that tipE and para gene products physically interact and the extent of synergistic interaction is determined by the nature and the location of mutation in the different para alleles. The cloning of tipE made it possible to study the direct interactions between para and tipE. Further analysis of molecular lesions in the different para alleles, combined with site-directed mutagenesis, may help to understand the mechanism and site of the interaction between tipE and para gene products.

3. Function of Truncated Protein in tipE Mutants.

Sequence of genomic DNA from tipE mutants revealed a point mutation causing a premature stop codon in the open reading frame of tipE gene. The truncated protein has the first transmembrane domain and most of the large extracellular loop which is properly translocated when in vitro translated. Studies using germline transformation with this mutant cDNA under the control of heat shock promoter, presented herein, showed that overexpression of the truncated protein, although failing to rescue the paralytic phenotype, partially rescues the heat-induced lethality in adult tipE flies. This result suggests that the truncated protein has residual function in tipE flies, and, therefore, that the tipE mutation is a hypomorph.

Although the translocation in T(2;3)TE2 is accompanied by a 2.5 kb deletion at the 5' end of the tipE gene, it only affects the upstream regulatory region and the 5' untranslated region of tipE gene, not the open reading frame. The cytogenetic localization experiments presented herein demonstrate that all three alternatively spliced forms of tipE transcripts are still expressed in T(2;3)TE2 flies, but with smaller sizes and presumably with different expression patterns because of disruption of the upstream regulatory region. Thus the null phenotype of tipE is unknown.

Although the invention has been described in detail for the purpose of illustration, it is understood that such detail is solely for that purpose, and variations can be made therein by those skilled in the art without departing from the spirit and scope of the invention which is described by the following claims.

---

What is claimed is:

1. A method of identifying agents which modulate an ion channel comprising:

transforming a host cell with a first nucleic acid encoding tipE protein from *Drosophilia melanogaster* and a second nucleic acid encoding a para protein;

facilitating co-expression of said first and second nucleic acids in said host cell, thereby forming a functional voltage dependent cation channel in said cell;

exposing said cell to an agent; and evaluating whether the agent affects the activity of the voltage dependent cation channel.

2. A method according to claim 1, wherein the agent is a pesticide.

3. A method according to claim 1, wherein the agent is identified as a candidate pesticide for the control of *Drosophila melanogaster*.

4. A method according to claim 1, wherein the para protein is a Drosophila para protein.

5. A method according to claim 1, wherein the tipE protein from *Drosophila melanogaster* comprises the amino acid sequence set forth in SEQ. ID. No. 2.

6. A method according to claim 5, wherein the nucleic acid encoding tipE protein comprises the nucleotide sequence set forth in SEQ. ID. No. 4.

7. A method according to claim 1, wherein said evaluating comprises measuring cation current in the functional voltage dependent cation channel.

8. A method of identifying agents which modulate an ion channel comprising:

providing a host cell comprising a first nucleic acid encoding a heterologous *Drosophila melanogaster* tipE protein and a second nucleic acid molecule encoding a para protein, wherein the amino acid sequences of said tipE protein is encoded by a cDNA isolated from a *Drosophila melanogaster* library and wherein the concomitant expression of said tipE protein and said para protein in a host cell affords detectable cation channel activity, which activity is not detectable when said para protein is expressed in the absence of said tipE protein;

culturing the host cell under conditions suitable for the concomitant expression of the translation products of said first and second nucleic acids in said host cell to produce a voltage dependent cation channel in said host cell;

exposing said host cell to an agent; and evaluating whether the agent affects the activity of the voltage dependent cation channel.

9. A method according to claim 8, wherein the agent is a pesticide.

10. A method according to claim 8, wherein the agent is identified as a candidate pesticide for the control of *Drosophila melanogaster*.

11. A method according to claim 8, wherein the tipE protein from *Drosophila melanogaster* comprises the amino acid sequence set forth in SEQ. ID. No. 2.

12. A method according to claim 11, wherein the nucleic acid encoding tipE protein comprises the nucleotide sequence set forth in SEQ. ID. No. 4.

13. A method according to claim 1, wherein said evaluating comprises measuring cation current in the voltage dependent cation channel.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 3954 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATTGTTGCCA CTAAAGAAAG GCAAGAGGAA CCGAAAATGC CACGAAAGAA AATGTGGAGC      60
GTGAATGTGA CAATTGTTCA GCGTTAGAAC TTTTGACCCC GTGCGCAATC AGGTCACCAT     120
TGTTCCATGC CTTTGTGAAC TGCACGTGGC AAGGATAGAA AGGAGAAGAA GAGAAGGAAA     180
GAGCATGCTG GAGAGAGAGG AAGAGTGCTA GGAATAGCCA ACCAAAGCAA AAAAGTGAAA     240
AAGACAAACA AAACTGTCCG TCCAGCATTC GTTTTCTAC  ACACATTTCG AAAGAATGTA     300
AATGTAAAGT GAAGAAAAAC AGAGAGTAAG AGAGAGACCT CAAAACTGGC CATTGGCAGG     360
CCAAACACAT ACACAGGCAC ACCAAGCATA CAGGACACAC AGGCCACACA CGACACACAC     420
GCACGAACAT CCAGTGCTTT GCCGCAGTCA TAAATAATC  AAGAAGCAGC TAAATCAGGC     480
AAAAGCAAGA CGACTGCAAC GTGCTGATGT TGACGAAACA TCTCCATTGG GACGAATAAA     540
GCAATTAGCA AAGGTTCACG ATTGTTGCCA CCACACTGCC AGGAGGCGGA GGAAGCTGGA     600
GGGGATTAAG AATGCGGGAT ACGTGGGACT CGCACTCGGA CTCCGTGGAG TATTTAGCCT     660
AATCGAGTGA AGCGATGCCG TTGAACTGGA GCACAAAGAT GCAGGACCCT CCCTGCAAAG     720
GTCAGCTATG TGCGAGATAA CGGGACACCG GACAGCCAGG CAACCAAAGC GAAAGAAGCA     780
AAAGCAGAAG CAACAGCAAA AGCAAACGAA ACGAGAAATC GAACTCTCCC TGTGATATAA     840
CTTGCACCGT AATCGTAATC TAGCTATTAG TTATCGTTAT CGATCAGTAA TCGCCGCAAT     900
TGTAAGCTAA GTTATCGCAC TTATCGCCGC TCTGCTCCGC CGCCGCCACC GCCAGACCTG     960
CGCCTAAAAA CTAATAATAT TAATAAAATT AAATAATACC ATAATATATA GTAGACCTCA    1020
AACCCGACCA AAATCGAGCT AAAACATGGG AGACGAGCAG GACAAACGCA CCGGCAAGGA    1080
GAAGCTGCTC TTCTACACCA CCGCCTTCTT CATCCTGCTG GGCACCTTCA GCCTGTTCGC    1140
CTTCCTCTTC CTGGTGCCCT TCGTCATCGA GCCCGCCTTC ACCACGATCT TCATGCAGTT    1200
CGAGGAGGTT CCGGCGCTCT GCGAAACGTA CGACACGGAG ATCTACTACG GGCCAAGAA     1260
CTGTTCGTGG TCGTCCTGCC GCGAGGGCTG CACCAAGGAC ATCTATACGT GCACCCAGAT    1320
TCGGGTGAAC TACCGTCTCA ATCTATATAA CTTCACCGAT GAGTTCAACT TCACGGAGTA    1380
CCACATCAAT CTCAAGGAGG CGGAGCGCAT CCTGCCGCCC GTCAAGCGAA CGGATCGCTA    1440
TGAGAGAGCT CTGAGGAGCG ACTACGAGTA CGATAATCTG GGTGGTGGCA CCGGCTTGGA    1500
CATCGACTTA GGCGCCGGCC GGATGGAACA GCTCAATTTT GGGGATGCCG ACGGCTCCAA    1560
TGGCTACCTC ATTGAGGATT CGGAGGATAC GCGCGGTCTG AGCGCTTCGG GTACCCTCAT    1620
TTCGGACGAG CGGAGGCCGT TCGACGAGAT CTCCGAGCTG AACGAGGGCC TGATGGGGAA    1680
CCGCTCCATG TACTACTATG TGGGAGCCAG GCTCTTTCCG AATGTAAAGG GCTGTGGCTA    1740
CCCGCCAATG CTCAACTGTA CCATCTGGCT AAAGAGGTAC ACCAAGATCG GCATGAAGTT    1800
CCCCTGCTAC TACTCCAAGG TGGACCCAAG TCTGGTCATC AGCGACCTGG ACTACTGGCA    1860
GAACACCCTA AACTTGGTCT ACTCGATGGC CATTCCAATA CCCTCGTTCA TCATCTCGGT    1920
GATTTATCTG ACGTATGCCT ACTTCAAGAT ATACAACGAG GATGAGGAGA CGGCGCCGTT    1980
GGACAAGAAC GCCGAAGACA TGGACATCGA TGATATCGAT GCCGTGGACG ACAGCGATGG    2040
TGCAGTCCTG GCGGACAATG TGGCCGGTAG CCAAATCATT AACATGGACT CAACCACCAA    2100
CGACAGTTGT CTGGAGGGTG TCCTGCCCAA CGGCGGTCCC GGCATGACCG CCTCCATATC    2160
GCAGGGTGGC TCCGTCACCA CGCCGGGTCC GTACATCGCG CAGAGTCCGG CGGGCTCGCA    2220
GATGACGCCC AACTCGGAGA TCAACTCGTT CGGTCACCAG CTGAAAGTCC AGATGGCCGA    2280
CGAGCTATCG AGGGATTCGC TGGAGAACGG AGCTATCTCC ACGTCCAACT CAGTGCAAGG    2340
```

```
AAACTTGAGC AAGACGATGA CGACGAGTAT CTCAACTCCT CCTGGGCCGA CAGCGGCAGT    2400
CTGAAACGTC AGGCGCATGG TCTGGAAAAT GTTAGATTCC GATTCAGAAA ATGAGCCGCT    2460
ACTGGACTCG TAGACCGCCG AGCGGTCAGC CACGGACCAC GGAGCAGGCG GAGATCACCG    2520
GAGCGGAGAC CCAACCCGAA AAAGAACTCA TGAGGCAACC GTAAAGCGCG ATACACCCCA    2580
AGTATTTCTA CCCGAAACAA TCGACAACAA CGCAGCGAAT GCGACCGAAC CTGAATACCT    2640
TCAGAGCTGT TAGCGGCACC TAATGAACTA TGATAGATTA TATTTACCTT ATGAACTAGC    2700
TACTCGGATT CACACCTACA CTCACACAAA CACTCACCCA CATTAAGCAC GCTAGATAGC    2760
CGGAGTAACT CCGGACTGCC ACACCCACTC AAAATTGCAA TGCACGGGCA TTATAGTATG    2820
TGCACAGTAT CTGATATCTG GAGGATCTTA GGCGATTGGT ACAAATACAA TAAAAACATA    2880
GGCCGCATGG ACTCGAGCAT GGAGTGCTAT TCATATACCT AGAGGAAAAA CTATAATACT    2940
TATACACGCA TATACAAATA TTTACTTGAA TTATTTTTCT ATTCGCAACA ATCGTCGTCG    3000
TCTCGAGGCA GAAACACAGA TAAACTCCAC CAACTCCACT ACCCCACTAC CCATTGCCCA    3060
ACATCCACAA TCCAAACAC AAATTCCAAA TAGAGCAAAT AAAAGCAAAA GAAAACAAG     3120
GCGCGCAACT TATTTACAAA TCGATAAATC GAGGCGCTGA GGTTTTTAA ATATTGTAAT    3180
GCCCATTCAA GTGCTGCAAA CCGTAATGCG TAAAAACCGA AAAACAGAAA TTAAATTTAA    3240
CAACAAACGA AAGCATCGTG TATTTCATTT AAACGTAATG ATAAACGAAA GCAAGTCGAA    3300
TGCCTATATT TGAAGTAAAT TAAATTAAAT TAAATTAACA TTAACTTAAA TTAACGTAAA    3360
TTAACTAACA TTGTTATCCT TCAAATTAAT GCGGATAAAA ACTCACAGCT TTAACTAACT    3420
GAAACGGAGG CATAAGATTT TCCTTCTACA TATTTATTTT ATTAAGATTA TTAACGGATA    3480
GTGAATATTT ATAGGTCCTA CAAATGGTTC AAGCTATTCA ATTAAAAACT TACAAATAAA    3540
ATATTGCATT AAATCTTAAT AATTTAGGTC TGAAATTAAA TATAAACTAA CGTTTCCTTT    3600
TTATATTACA AACAAAACCG AAAACCAAAC CAAGTCACTT CTAAACGAAA TTGCGTATAG    3660
AATGCGTATA GAAGCATCCG CATCTGCATC AGCATCCGCA TCCGCATCAA TAAACTGCAC    3720
TTTTGCGCAT ATTGTATCAA TGATAGGCGG CAATGAACTA CACAGAAATC GTTTGTTTTT    3780
AACGACAGTT GGAAATAGTT AACGAGGGTC AAGCAATGGC AACAGAAGCG CAACTATTAG    3840
CTAATATCAT GTAAAACAGA CAAACAAATA ACAAATGCT ACTAGAATTG AAACCAAATA     3900
CATGAAAATC TCGAAATAAA TACGCATTTA GCAGCCTAAA AAAAAAAAA AAAA           3954
```

(2) INFORMATION FOR SEQ ID NO:2:

(i) SEQUENCE CHARACTERISTICS:
        (A) LENGTH: 452 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gly Asp Glu Gln Asp Lys Arg Thr Gly Lys Glu Lys Leu Leu Phe
 1               5                  10                  15

Tyr Thr Thr Ala Phe Phe Ile Leu Leu Gly Thr Phe Ser Leu Phe Ala
            20                  25                  30

Phe Leu Phe Leu Val Pro Phe Val Ile Glu Pro Ala Phe Thr Thr Ile
        35                  40                  45

Phe Met Gln Phe Glu Glu Val Pro Ala Leu Cys Glu Thr Tyr Asp Thr
    50                  55                  60
```

```
Glu  Ile  Tyr  Tyr  Gly  Ala  Lys  Asn  Cys  Ser  Trp  Ser  Ser  Cys  Arg  Glu
 65            70                      75                      80

Gly  Cys  Thr  Lys  Asp  Ile  Tyr  Thr  Cys  Thr  Gln  Ile  Arg  Val  Asn  Tyr
               85                      90                      95

Arg  Leu  Asn  Leu  Tyr  Asn  Phe  Thr  Asp  Glu  Phe  Asn  Phe  Thr  Glu  Tyr
              100                     105                     110

His  Ile  Asn  Leu  Lys  Glu  Ala  Glu  Arg  Ile  Leu  Pro  Pro  Val  Lys  Arg
              115                     120                     125

Thr  Asp  Arg  Tyr  Glu  Arg  Ala  Leu  Arg  Ser  Asp  Tyr  Glu  Tyr  Asp  Asn
         130                     135                     140

Leu  Gly  Gly  Gly  Thr  Gly  Leu  Asp  Ile  Asp  Leu  Gly  Ala  Gly  Arg  Met
145                          150                     155                     160

Glu  Gln  Leu  Asn  Phe  Gly  Asp  Ala  Asp  Gly  Ser  Asn  Gly  Tyr  Leu  Ile
              165                     170                     175

Glu  Asp  Ser  Glu  Asp  Thr  Arg  Gly  Leu  Ser  Ala  Ser  Gly  Thr  Leu  Ile
              180                     185                     190

Ser  Asp  Glu  Arg  Arg  Pro  Phe  Asp  Glu  Ile  Ser  Glu  Leu  Asn  Glu  Gly
              195                     200                     205

Leu  Met  Gly  Asn  Arg  Ser  Met  Tyr  Tyr  Tyr  Val  Gly  Ala  Arg  Leu  Phe
     210                     215                     220

Pro  Asn  Val  Lys  Gly  Cys  Gly  Tyr  Pro  Pro  Met  Leu  Asn  Cys  Thr  Ile
225                          230                     235                     240

Trp  Leu  Lys  Arg  Tyr  Thr  Lys  Ile  Gly  Met  Lys  Phe  Pro  Cys  Tyr  Tyr
                    245                     250                     255

Ser  Lys  Val  Asp  Pro  Ser  Leu  Val  Ile  Ser  Asp  Leu  Asp  Tyr  Trp  Gln
               260                     265                     270

Asn  Thr  Leu  Asn  Leu  Val  Tyr  Ser  Met  Ala  Ile  Pro  Ile  Pro  Ser  Phe
               275                     280                     285

Ile  Ile  Ser  Val  Ile  Tyr  Leu  Thr  Tyr  Ala  Tyr  Phe  Lys  Ile  Tyr  Asn
          290                     295                     300

Glu  Asp  Glu  Glu  Thr  Ala  Pro  Leu  Asp  Lys  Asn  Ala  Glu  Asp  Met  Asp
305                          310                     315                     320

Ile  Asp  Asp  Ile  Asp  Ala  Val  Asp  Asp  Ser  Asp  Gly  Ala  Val  Leu  Ala
                    325                     330                     335

Asp  Asn  Val  Ala  Gly  Ser  Gln  Ile  Ile  Asn  Met  Asp  Ser  Thr  Thr  Asn
               340                     345                     350

Asp  Ser  Cys  Leu  Glu  Gly  Val  Leu  Pro  Asn  Gly  Gly  Pro  Gly  Met  Thr
          355                     360                     365

Ala  Ser  Ile  Ser  Gln  Gly  Gly  Ser  Val  Thr  Thr  Pro  Gly  Pro  Tyr  Ile
     370                     375                     380

Ala  Gln  Ser  Pro  Ala  Gly  Ser  Gln  Met  Thr  Pro  Asn  Ser  Glu  Ile  Asn
385                          390                     395                     400

Ser  Phe  Gly  His  Gln  Leu  Lys  Val  Gln  Met  Ala  Asp  Glu  Leu  Ser  Arg
                    405                     410                     415

Asp  Ser  Leu  Glu  Asn  Gly  Ala  Ile  Ser  Thr  Ser  Asn  Ser  Val  Gln  Gly
               420                     425                     430

Asn  Leu  Ser  Lys  Thr  Met  Thr  Thr  Ser  Ile  Ser  Thr  Pro  Gly  Pro
               435                     440                     445

Thr  Ala  Ala  Val
                450
```

( 2 ) INFORMATION FOR SEQ ID NO:3:

( i ) SEQUENCE CHARACTERISTICS:
        ( A ) LENGTH: 1045 base pairs

-continued (B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:3:

| | | | | | | |
|---|---|---|---|---|---|---|
| ATTGTTGCCA | CTAAAGAAAG | GCAAGAGGAA | CCGAAAATGC | CACGAAAGAA | AATGTGGAGC | 60 |
| GTGAATGTGA | CAATTGTTCA | GCGTTAGAAC | TTTTGACCCC | GTGCGCAATC | AGGTCACCAT | 120 |
| TGTTCCATGC | CTTTGTGAAC | TGCACGTGGC | AAGGATAGAA | AGGAGAAGAA | GAGAAGGAAA | 180 |
| GAGCATGCTG | GAGAGAGAGG | AAGAGTGCTA | GGAATAGCCA | ACCAAAGCAA | AAAAGTGAAA | 240 |
| AAGACAAACA | AAACTGTCCG | TCCAGCATTC | GTTTTTCTAC | ACACATTTCG | AAAGAATGTA | 300 |
| AATGTAAAGT | GAAGAAAAAC | AGAGAGTAAG | AGAGAGACCT | CAAAACTGGC | CATTGGCAGG | 360 |
| CCAAACACAT | ACACAGGCAC | ACCAAGCATA | CAGGACACAC | AGGCCACACA | CGACACACAC | 420 |
| GCACGAACAT | CCAGTGCTTT | GCCGCAGTCA | TAAAATAATC | AAGAAGCAGC | TAAATCAGGC | 480 |
| AAAAGCAAGA | CGACTGCAAC | GTGCTGATGT | TGACGAAACA | TCTCCATTGG | GACGAATAAA | 540 |
| GCAATTAGCA | AAGGTTCACG | ATTGTTGCCA | CCACACTGCC | AGGAGGCGGA | GGAAGCTGGA | 600 |
| GGGGATTAAG | AATGCGGGAT | ACGTGGGACT | CGCACTCGGA | CTCCGTGGAG | TATTTAGCCT | 660 |
| AATCGAGTGA | AGCGATGCCG | TTGAACTGGA | GCACAAAGAT | GCAGGACCCT | CCCTGCAAAG | 720 |
| GTCAGCTATG | TGCGAGATAA | CGGGACACCG | GACAGCCAGG | CAACCAAAGC | GAAAGAAGCA | 780 |
| AAAGCAGAAG | CAACAGCAAA | AGCAAACGAA | ACGAGAAATC | GAACTCTCCC | TGTGATATAA | 840 |
| CTTGCACCGT | AATCGTAATC | TAGCTATTAG | TTATCGTTAT | CGATCAGTAA | TCGCCGCAAT | 900 |
| TGTAAGCTAA | GTTATCGCAC | TTATCGCCGC | TCTGCTCCGC | CGCCGCCACC | GCCAGACCTG | 960 |
| CGCCTAAAAA | CTAATAATAT | TAATAAAATT | AAATAATACC | ATAATATATA | GTAGACCTCA | 1020 |
| AACCCGACCA | AAATCGAGCT | AAAAC | | | | 1045 |

(2) INFORMATION FOR SEQ ID NO:4:

(i) SEQUENCE CHARACTERISTICS:
(A) LENGTH: 1356 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:4:

| | | | | | | |
|---|---|---|---|---|---|---|
| ATGGGAGACG | AGCAGGACAA | ACGCACCGGC | AAGGAGAAGC | TGCTCTTCTA | CACCACCGCC | 60 |
| TTCTTCATCC | TGCTGGGCAC | CTTCAGCCTG | TTCGCCTTCC | TCTTCCTGGT | GCCCTTCGTC | 120 |
| ATCGAGCCCG | CCTTCACCAC | GATCTTCATG | CAGTTCGAGG | AGGTTCCGGC | GCTCTGCGAA | 180 |
| ACGTACGACA | CGGAGATCTA | CTACGGGGCC | AAGAACTGTT | CGTGGTCGTC | CTGCCGCGAG | 240 |
| GGCTGCACCA | AGGACATCTA | TACGTGCACC | CAGATTCGGG | TGAACTACCG | TCTCAATCTA | 300 |
| TATAACTTCA | CCGATGAGTT | CAACTTCACG | GAGTACCACA | TCAATCTCAA | GGAGGCGGAG | 360 |
| CGCATCCTGC | CGCCCGTCAA | GCGAACGGAT | CGCTATGAGA | GAGCTCTGAG | GAGCGACTAC | 420 |
| GAGTACGATA | ATCTGGGTGG | TGGCACCGGC | TTGGACATCG | ACTTAGGCGC | CGGCCGGATG | 480 |
| GAACAGCTCA | ATTTTGGGGA | TGCCGACGGC | TCCAATGGCT | ACCTCATTGA | GGATTCGGAG | 540 |
| GATACGCGCG | GTCTGAGCGC | TTCGGGTACC | CTCATTTCGG | ACGAGCGGAG | GCCGTTCGAC | 600 |
| GAGATCTCCG | AGCTGAACGA | GGGCCTGATG | GGAACCGCT | CCATGTACTA | CTATGTGGGA | 660 |
| GCCAGGCTCT | TTCCGAATGT | AAAGGGCTGT | GGCTACCCGC | CAATGCTCAA | CTGTACCATC | 720 |

| | | | | | |
|---|---|---|---|---|---|
| TGGCTAAAGA | GGTACACCAA | GATCGGCATG | AAGTTCCCCT | GCTACTACTC | CAAGGTGGAC | 780
| CCAAGTCTGG | TCATCAGCGA | CCTGGACTAC | TGGCAGAACA | CCCTAAACTT | GGTCTACTCG | 840
| ATGGCCATTC | CAATACCCTC | GTTCATCATC | TCGGTGATTT | ATCTGACGTA | TGCCTACTTC | 900
| AAGATATACA | ACGAGGATGA | GGAGACGGCG | CCGTTGGACA | AGAACGCCGA | AGACATGGAC | 960
| ATCGATGATA | TCGATGCCGT | GGACGACAGC | GATGGTGCAG | TCCTGGCGGA | CAATGTGGCC | 1020
| GGTAGCCAAA | TCATTAACAT | GGACTCAACC | ACCAACGACA | GTTGTCTGGA | GGGTGTCCTG | 1080
| CCCAACGGCG | GTCCCGGCAT | GACCGCCTCC | ATATCGCAGG | GTGGCTCCGT | CACCACGCCG | 1140
| GGTCCGTACA | TCGCGCAGAG | TCCGGCGGGC | TCGCAGATGA | CGCCCAACTC | GGAGATCAAC | 1200
| TCGTTCGGTC | ACCAGCTGAA | AGTCCAGATG | GCCGACGAGC | TATCGAGGGA | TTCGCTGGAG | 1260
| AACGGAGCTA | TCTCCACGTC | CAACTCAGTG | CAAGGAAACT | TGAGCAAGAC | GATGACGACG | 1320
| AGTATCTCAA | CTCCTCCTGG | GCCGACAGCG | GCAGTC | | | 1356

( 2 ) INFORMATION FOR SEQ ID NO:5:

( i ) SEQUENCE CHARACTERISTICS:
        ( A ) LENGTH: 1549 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| TGAAACGTCA | GGCGCATGGT | CTGGAAAATG | TTAGATTCCG | ATTCAGAAAA | TGAGCCGCTA | 60
| CTGGACTCGT | AGACCGCCGA | GCGGTCAGCC | ACGGACCACG | GAGCAGGCGG | AGATCACCGG | 120
| AGCGGAGACC | CAACCCGAAA | AAGAACTCAT | GAGGCAACCG | TAAAGCGCGA | TACACCCCAA | 180
| GTATTTCTAC | CCGAAACAAT | CGACAACAAC | GCAGCGAATG | CGACCGAACC | TGAATACCTT | 240
| CAGAGCTGTT | AGCGGCACCT | AATGAACTAT | GATAGATTAT | ATTTACCTTA | TGAACTAGCT | 300
| ACTCGGATTC | ACACCTACAC | TCACACAAAC | ACTCACCCAC | ATTAAGCACG | CTAGATAGCC | 360
| GGAGTAACTC | CGGACTGCCA | CACCCACTCA | AAATTGCAAT | GCACGGGCAT | TATAGTATGT | 420
| GCACAGTATC | TGATATCTGG | AGGATCTTAG | GCGATTGGTA | CAAATACAAT | AAAAACATAG | 480
| GCCGCATGGA | CTCGAGCATG | GAGTGCTATT | CATATACCTA | GAGGAAAAAC | TATAATACTT | 540
| ATACACGCAT | ATACAAATAT | TTACTTGAAT | TATTTTTCTA | TTCGCAACAA | TCGTCGTCGT | 600
| CTCGAGGCAG | AAACACAGAT | AAACTCCACC | AACTCCACTA | CCCCACTACC | CATTGCCCAA | 660
| CATCCACAAT | CCAAAACACA | AATTCCAAAT | AGAGCAAATA | AAAGCAAAAG | AAAAACAAGG | 720
| CGCGCAACTT | ATTTACAAAT | CGATAAATCG | AGGCGCTGAG | GTTTTTAAA | TATTGTAATG | 780
| CCCATTCAAG | TGCTGCAAAC | CGTAATGCGT | AAAAACCGAA | AAACAGAAAT | TAAATTTAAC | 840
| AACAAACGAA | AGCATCGTGT | ATTTCATTTA | AACGTAATGA | TAAACGAAAG | CAAGTCGAAT | 900
| GCCTATATTT | GAAGTAAATT | AAATTAAATT | AAATTAACAT | TAACTTAAAT | TAACGTAAAT | 960
| TAACTAACAT | TGTTATCCTT | CAAATTAATG | CGGATAAAAA | CTCACAGCTT | TAACTAACTG | 1020
| AAACGGAGGC | ATAAGATTTT | CCTTCTACAT | ATTTATTTTA | TTAAGATTAT | TAACGGATAG | 1080
| TGAATATTTA | TAGGTCCTAC | AAATGGTTCA | AGCTATTCAA | TTAAAAACTT | ACAAATAAAA | 1140
| TATTGCATTA | AATCTTAATA | ATTTAGGTCT | GAAATTAAAT | ATAAACTAAC | GTTTCCTTTT | 1200
| TATATTACAA | ACAAAACCGA | AAACCAAACC | AAGTCACTTC | TAAACGAAAT | TGCGTATAGA | 1260
| ATGCGTATAG | AAGCATCCGC | ATCTGCATCA | GCATCCGCAT | CCGCATCAAT | AAACTGCACT | 1320

-continued

| | | | | | | |
|---|---|---|---|---|---|---|
| TTTGCGCATA | TTGTATCAAT | GATAGGCGGC | AATGAACTAC | ACAGAAATCG | TTTGTTTTTA | 1380 |
| ACGACAGTTG | GAAATAGTTA | ACGAGGGTCA | AGCAATGGCA | ACAGAAGCGC | AACTATTAGC | 1440 |
| TAATATCATG | TAAAACAGAC | AAACAAATAA | CAAATGCTA | CTAGAATTGA | AACCAAATAC | 1500 |
| ATGAAAATCT | CGAAATAAAT | ACGCATTTAG | CAGCCTAAAA | AAAAAAAA | | 1549 |